US009239517B2

(12) United States Patent
Echigo

(10) Patent No.: US 9,239,517 B2
(45) Date of Patent: Jan. 19, 2016

(54) COMPOUND, RADIATION-SENSITIVE COMPOSITION AND RESIST PATTERN FORMATION METHOD

(75) Inventor: Masatoshi Echigo, Kanagawa (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 79 days.

(21) Appl. No.: 13/812,831

(22) PCT Filed: Jul. 25, 2011

(86) PCT No.: PCT/JP2011/004179
§ 371 (c)(1),
(2), (4) Date: Jan. 28, 2013

(87) PCT Pub. No.: WO2012/014435
PCT Pub. Date: Feb. 2, 2012

(65) Prior Publication Data
US 2013/0122423 A1    May 16, 2013

(30) Foreign Application Priority Data
Jul. 30, 2010    (JP) ................................. 2010-172403

(51) Int. Cl.
*G03F 7/004*    (2006.01)
*G03F 7/039*    (2006.01)
*C07C 43/307*    (2006.01)
*C07C 69/76*    (2006.01)
*G03F 7/20*    (2006.01)

(52) U.S. Cl.
CPC .............. *G03F 7/004* (2013.01); *C07C 43/307* (2013.01); *C07C 69/76* (2013.01); *G03F 7/0045* (2013.01); *G03F 7/0392* (2013.01); *G03F 7/0397* (2013.01); *G03F 7/20* (2013.01)

(58) Field of Classification Search
CPC ......... G03F 7/004; G03F 7/045; C07C 33/26; C07C 33/36; C07C 33/38; C07C 43/307; C07C 69/76
USPC .......... 430/270.1; 524/6, 7; 528/86; 568/717, 568/718, 720, 721
See application file for complete search history.

(56) References Cited

U.S. PATENT DOCUMENTS

| 4,259,464 | A | * | 3/1981 | Buriks et al. | 525/480 |
| 4,699,966 | A | * | 10/1987 | Harris et al. | 528/12 |
| 6,174,503 | B1 | * | 1/2001 | Moyer et al. | 423/181 |
| 2007/0217965 | A1 | * | 9/2007 | Johnson et al. | 422/139 |
| 2010/0227095 | A1 | * | 9/2010 | Miyauchi et al. | 428/36.8 |
| 2011/0130307 | A1 | * | 6/2011 | Takahashi et al. | 506/16 |
| 2012/0171615 | A1 | * | 7/2012 | Echigo et al. | 430/281.1 |

FOREIGN PATENT DOCUMENTS

| JP | 2-53749 | A | | 2/1990 |
| JP | H2-53749 | A | | 2/1990 |
| JP | 2-124850 | A | | 5/1990 |
| JP | 9-263560 | | | 10/1997 |
| JP | 9-263560 | A | | 10/1997 |
| JP | 11-43524 | A | | 2/1999 |
| JP | 11-322656 | A | | 11/1999 |
| JP | 11-344808 | A | | 12/1999 |
| JP | 2000-98613 | A | | 4/2000 |
| JP | 2004-18421 | A | | 1/2004 |
| JP | 2005-308977 | A | | 11/2005 |
| JP | 2006-2073 | A | | 1/2006 |
| JP | 2006-3846 | A | | 1/2006 |
| JP | 2006-16342 | A | | 1/2006 |
| JP | 2006-248979 | | * | 9/2006 |
| JP | 2007-206371 | A | | 8/2007 |
| JP | 2008-56675 | A | | 3/2008 |
| JP | 2009-173623 | A | | 8/2009 |
| JP | 2009-244769 | | | 10/2009 |
| JP | 2009-244769 | A | | 10/2009 |
| JP | 2010-138109 | A | | 6/2010 |
| WO | WO 2011/024916 | | * | 3/2011 |

OTHER PUBLICATIONS

Machine translation of JP 2006-248979, published on Sep. 21, 2006.*
International Search Report from the International Bureau of WIPO for International Application No. PCT/JP2011/004179 dated Aug. 30, 2011 and English translation of the same (4 pages).
Office Action issued for Chinese Application No. 201180038193.4 dated Aug. 20, 2014 and English translation of the same.
Japanese Office Action dated Feb. 24, 2015 for Japanese Patent Application 2012-526304 and English translation of the same (12 pages).
Chinese Office Action dated Apr. 1, 2015 for Chinese Patent Application 201180038193.4 and English translation of the same (13 pages).
Taiwanese Office Action dated Nov. 19, 2014 for Taiwanese Patent Application 100126775 and English translation of the same (7 pages).
Taiwanese Office Action dated Apr. 22, 2015 for Taiwanese Patent Application 100126775 and English translation of the same.
Chinese Office Action dated Jul. 9, 2015 for Chinese Patent Application 201180038193.4 and English translation of the same. (8 pages).

* cited by examiner

*Primary Examiner* — Anca Eoff
(74) *Attorney, Agent, or Firm* — Fitch Even Tabin & Flannery LLP

(57) ABSTRACT

The object is to provide a compound having high dissolvability in a safe solvent and high sensitivity, and also capable of obtaining a good resist pattern shape, a radiation-sensitive composition containing the same, and a resist pattern formation method using the composition. For this purpose, a compound (B) obtained by reaction between a polyphenol based cyclic compound (A) and a compound (C) having a particular structure, a radiation-sensitive composition containing the same, and a resist pattern formation method using the composition are provided.

10 Claims, No Drawings

COMPOUND, RADIATION-SENSITIVE COMPOSITION AND RESIST PATTERN FORMATION METHOD

CROSS-REFERENCE TO A RELATED APPLICATIONS

This application is a U.S. national phase application filed under 35 U.S.C. §371 of International Application PCT/JP2011/004179, filed on Jul. 25, 2011, designating the United States, which claims priority from Japanese Application 2010-172403, filed on Jul. 30, 2010, which are hereby incorporated herein by reference in their entirety.

FIELD OF THE INVENTION

This invention relates to a compound useful as a resist material, a radiation-sensitive composition using the same, and a resist pattern formation method.

BACKGROUND OF THE INVENTION

Along with miniaturization of semiconductor devices, development of lithography process using extreme ultraviolet light (13.5 nm) or electron beam for example has been intensely progressed. As a base material for a chemically sensitized positive type resist corresponding thereto, a novolac type phenol based resin, a polyhydroxy styrene based resin, a methacrylic acid based resin, and the like which are high molecular weight types have been mainly considered. However, since a high molecular weight type has the molecular weight as large as about 10,000 to 100,000 and also wide molecular weight distribution, in lithography using a high molecular weight type resist, there is a problem in that roughness occurs on a fine pattern surface. Therefore recently, development of a polyphenol based compound and a calixarene compound as low molecular weight types having an acid dissociable functional group degradable by action of acid introduced therein has been actively carried out, and there is even a reported case where roughness on a fine pattern is reduced compared to a high molecular weight type. Also, as a low molecular weight type material, a calixarene compound, which has a rigid cyclic structure in the main backbone and sufficient heat resistance required to form a pattern, is considered as promising.

As an acid dissociable functional group, a monofunctional alkoxymethyl group, alkoxyethyl group and tertiary alkoxy group are mainly used. However, a compound having these introduced therein has a problem in that collapse is liable to occur in the resultant fine pattern (JP-A-2009-173623).

Moreover, with a view to reduction of roughness and prevention of pattern collapse in a pattern obtained by using a high molecular weight type material, studies of using a multifunctional acid dissociable functional group have also been active (JP-A-H11-344808, JP-A-2000-098613, JP-A-2005-308977, JP-A-2006-2073, JP-A-2006-3846 and JP-A-2007-206371). However, there is no example of a report to introduce a multifunctional acid dissociable functional group into a calixarene compound.

SUMMARY OF THE INVENTION

The object of the invention is to provide a compound, which has high dissolvability in a safe solvent, can prevent collapse of the resultant resist pattern, and can reduce roughness of the resist pattern, also a radiation-sensitive composition containing the same, and a resist pattern formation method using the radiation-sensitive composition.

As a result of devoted examinations to solve the above problems, the inventors have discovered that a compound having a particular structure can prevent collapse of a resist pattern and also realize a resist pattern with small roughness, and reached completion of the invention.

More specifically, the invention is as follows.

1. A compound (B) obtained by reaction between a polyphenol based cyclic compound (A) represented by the following formula (1) and a compound represented by the following formula (3).

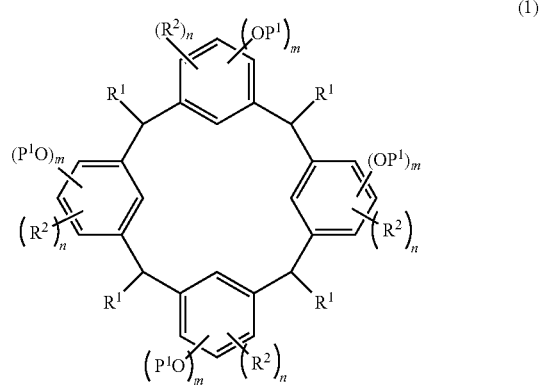

(In the formula (1), $R^1$ is independently a hydrogen atom, an alkyl group of 1 to 20 carbons, or a group represented by the following formula (2),

wherein, $R^2$ is independently a functional group selected from the group consisting of a hydrogen atom, an alkyl group of 1 to 20 carbons, a cycloalkyl group of 3 to 20 carbons, an aryl group of 6 to 20 carbons, an alkoxy group of 1 to 20 carbons, a hydroxyl group, a carboxyl group, a cyano group, a nitro group, a heterocyclic group, a halogen atom and an alkylsilyl group of 1 to 20 carbons, or an acid dissociable functional group selected from the group consisting of a substituted methyl group of 2 to 20 carbons, a 1-substituted ethyl group of 3 to 20 carbons, a 1-substituted-n-propyl group of 4 to 20 carbons, a 1-branched alkyl group of 3 to 20 carbons, a silyl group of 1 to 20 carbons, an acyl group of 2 to 20 carbons, a 1-substituted alkoxyalkyl group of 2 to 20 carbons, a cyclic ether group of 2 to 20 carbons, an alkoxycarbonyl group of 2 to 20 carbons and an alkoxycarbonylalkyl group, $P^1$ is independently a hydrogen atom or an alkyl group of 1 to 20 carbons, m is an integer of 1 to 4, n is an integer of 0 to 3, and p is an integer of 0 to 5, provided that the compound (A) has at least one phenolic hydroxyl group or carboxyl group.)

(In the formula (3), A is an aliphatic hydrocarbon group of 1 to 18 carbons, an alicyclic hydrocarbon group of 3 to 18 carbons or an aromatic hydrocarbon group of 6 to 24 carbons, B is an acid crosslinkable reactive group, and q is an integer of 2 to 4.)

2. A compound (B) according to the above item 1, wherein the acid crosslinkable reactive group is any one selected from the group consisting of a vinyloxy group, a halomethyl group, a halocarbonyl group and a carboxyl group.

3. A compound (B) according to the above item 1, wherein the compound (A) is a compound represented by the following formula (1-1).

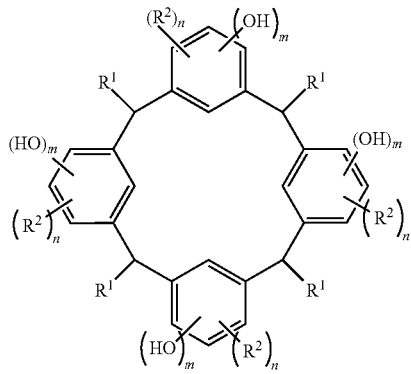

(1-1)

(In the formula (1-1), $R^1$, $R^2$, m and n are the same as above.)

4. A compound (B) according to the above item 3, wherein the compound (A) is a compound represented by the following formula (1-2).

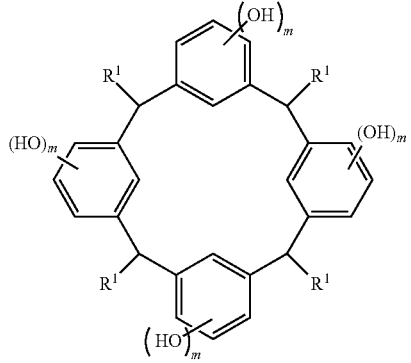

(1-2)

(In the formula (1-2), $R^1$ and m are the same as above.)

5. A compound (B) according to the above item 4, wherein the compound (A) is a compound represented by the following formula (1-3).

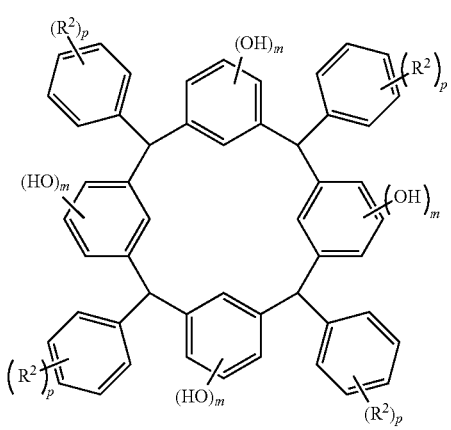

(1-3)

(In the formula (1-3), $R^2$, m and p are the same as above.)

6. A compound (B) according to the above item 5, wherein the compound (A) is a compound represented by the following formula (1-4) or (1-5).

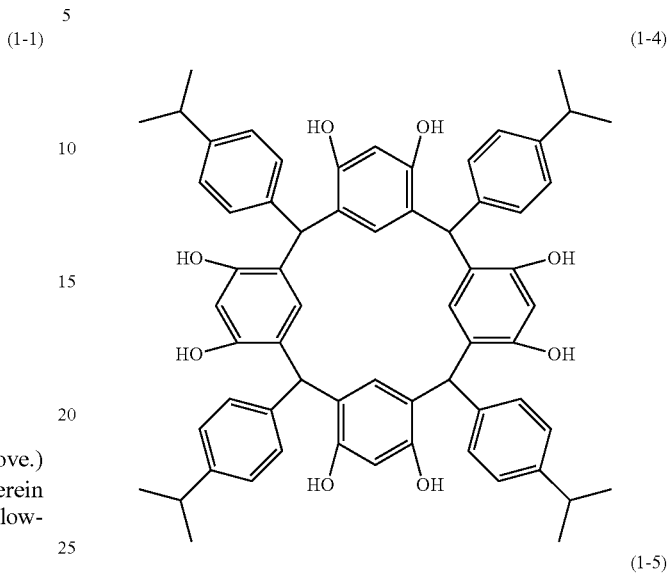

(1-4)

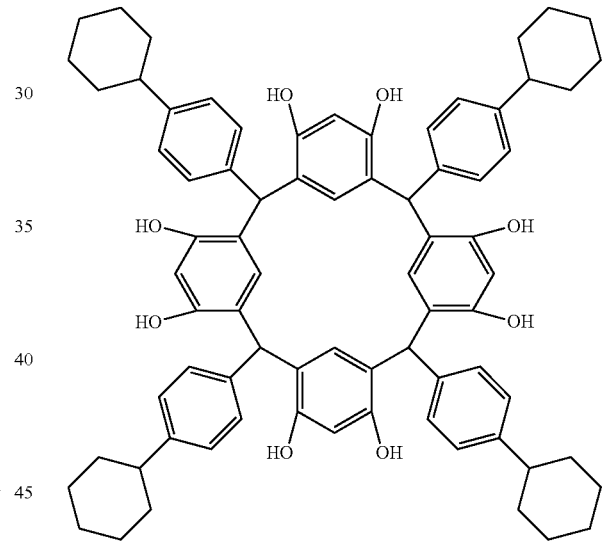

(1-5)

7. A compound (B) according to the above item 1, wherein the compound (C) is any compound selected from the compound group represented by the following formula (3-1).

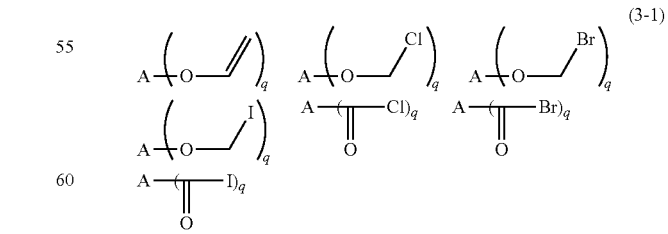

(3-1)

(In the formula (3-1), A and q are the same as above.)

8. A compound (B) according to the above item 7, wherein the compound (C) is any compound selected from the compound group represented by the following formula (3-2).

(In the formula (3-2), $n^1$ is an integer of 0 to 2, and q is an integer of 2 to 4.)

9. A compound (B) according to the above item 8, wherein the compound (C) is any compound selected from the compound group represented by the following formula (3-3).

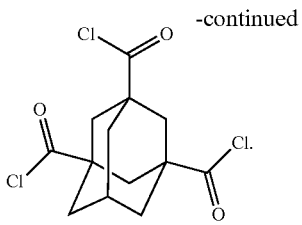

10. A positive type radiation-sensitive composition comprising a compound (B) according to any of the above items 1 to 9, an acid generator (D) generating acid directly or indirectly by irradiation of any radiation selected from the group consisting of visible light, ultraviolet light, excimer laser, electron beam, extreme ultraviolet light (EUV), X-ray and ion beam, an acid diffusion controller (E), and a solvent.

11. A positive type radiation-sensitive composition according to the above item 10, comprising 1 to 80% by weight of solid component and 20 to 99% by weight of solvent.

12. A resist pattern formation method comprising steps of forming a resist film on a substrate using a positive type radiation-sensitive composition according to the above item 10 or 11, exposing the resist film, and developing the resist film to form a resist pattern.

According to the invention, it is possible to provide a compound, which has high dissolvability in a safe solvent, can prevent collapse of the resultant resist pattern and can also reduce roughness, a positive type radiation-sensitive composition containing the same, and a resist pattern formation method using the radiation-sensitive composition.

DETAILED DESCRIPTION OF THE PREFERRED EMBODIMENTS

[Compound]

Below, the compound according to the invention will be descried in detail.

The invention is a compound (B) obtained by reaction between a polyphenol based cyclic compound (A) represented by the following formula (1) and a compound (C) represented by the following formula (3).

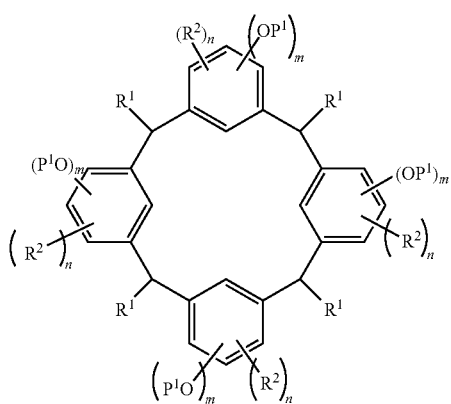

(In the formula (1), $R^1$ is independently a hydrogen atom, an alkyl group of 1 to 20 carbons, or a group represented by the following formula (2),

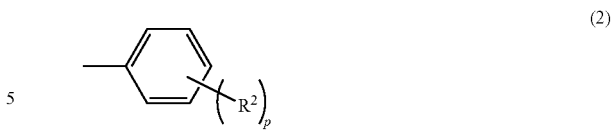

wherein, $R^2$ is independently a functional group selected from the group consisting of a hydrogen atom, an alkyl group of 1 to 20 carbons, a cycloalkyl group of 3 to 20 carbons, an aryl group of 6 to 20 carbons, an alkoxy group of 1 to 20 carbons, a hydroxyl group, a carboxyl group, a cyano group, a nitro group, a heterocyclic group, a halogen atom and an alkylsilyl group of 1 to 20 carbons, or an acid dissociable functional group selected from the group consisting of a substituted methyl group of 2 to 20 carbons, a 1-substituted ethyl group of 3 to 20 carbons, a 1-substituted-n-propyl group of 4 to 20 carbons, a 1-branched alkyl group of 3 to 20 carbons, a silyl group of 1 to 20 carbons, an acyl group of 2 to 20 carbons, a 1-substituted alkoxyalkyl group of 2 to 20 carbons, a cyclic ether group of 2 to 20 carbons, an alkoxycarbonyl group of 2 to 20 carbons and an alkoxycarbonylalkyl group, $P^1$ is independently a hydrogen atom or an alkyl group of 1 to 20 carbons, m is an integer of 1 to 4, n is an integer of 0 to 3, and p is an integer of 0 to 5, provided that the compound (A) has at least one phenolic hydroxyl group or carboxyl group.)

$$A\text{-}(B)_q \quad (3)$$

(In the formula (3), A is an aliphatic hydrocarbon group of 1 to 18 carbons, an alicyclic hydrocarbon group of 3 to 18 carbons or an aromatic hydrocarbon group of 6 to 24 carbons, B is an acid crosslinkable reactive group, and q is an integer of 2 to 4.)

As the alkyl group of 1 to 20 carbons, an alkyl group of 1 to 12 carbons is preferable, and an alkyl group of 1 to 6 carbons is more preferable. It can be exemplified by a methyl group, an ethyl group, a propyl group, a butyl group, a pentyl group, a hexyl group, a heptyl group, an octyl group, a decyl group, a dodecyl group, an undecyl group and the like.

As the cycloalkyl group of 3 to 20 carbons, a cycloalkyl group of 3 to 12 carbons is preferable, and a cycloalkyl group of 3 to 6 carbons is more preferable. It can be exemplified by a cyclopropyl group, a cyclobutyl group, a cyclopentyl group, a cyclohexyl group, a cycloheptyl group, a cyclooctyl group, a cyclodecyl group, a cyclododecyl group, a cycloundecyl group and the like.

As the aryl group of 6 to 20 carbons, an aryl group of 6 to 12 carbons is preferable, and an aryl group of 6 carbons is more preferable. It can be exemplified by a phenyl group, a naphthyl group, a biphenyl group, an anthracyl group, a phenantosyl group, a pyrenyl group and the like.

As the alkoxy group of 1 to 20 carbons, an alkoxy group of 1 to 12 carbons is preferable, and an alkoxy group of 1 to 6 carbons is more preferable. It can be exemplified by a methoxy group, an ethoxy group, a propoxy group, a butoxy group, a pentyloxy group, a hexyloxy group, a heptyloxy group, an octyloxy group, a decyloxy group, a dodecyloxy group, an undecyloxy group and the like.

As the heterocyclic group, a heterocyclic group of 1 to 12 carbons including a heterocyclic group containing 1 to 4 hetero atoms selected from the group consisting of N, O and S as a ring constituent atom is preferable, and a heterocyclic group of 1 to 6 carbons is more preferable. It can be exemplified by a quinolyl group, a 1,2,3,4-tetrahydroquinolyl group, a benzoimidazolyl group, a furyl group, a thienyl group, a thiazolyl group, a pyridyl group, a pyrimidyl group and the like.

The halogen atom can be exemplified by a fluoro group, a chloro group, a bromo group, an iodo group and the like.

As the alkylsilyl group of 1 to 20 carbons, an alkylsilyl group of 1 to 12 carbons is preferable, and an alkylsilyl group of 1 to 6 carbons is more preferable. It can be exemplified by a methylsilyl group, an ethylsilyl group, a propylsilyl group, a butylsilyl group, a pentylsilyl group, a hexylsilyl group, a heptylsilyl group, an octylsilyl group, a decylsilyl group, a dodecylsilyl group, an undecylsilyl group and the like.

The acid dissociable functional group can be arbitrarily selected from those suggested for a hydroxy styrene based resin, a methacrylic acid based resin and the like used in a chemically amplified resist composition for KrF or ArF, and used. It is preferably exemplified by a substituted methyl group, a 1-substituted ethyl group, a 1-substituted-n-propyl group, a 1-branched alkyl group, a silyl group, an acyl group, a 1-substituted alkoxymethyl group, a cyclic ether group, an alkoxycarbonyl group and the like. The acid dissociable functional group is preferable not to have a crosslinkable functional group.

As the substituted methyl group, a substituted methyl group of 2 to 20 carbons is normal, a substituted methyl group of 4 to 18 carbons is preferable, and a substituted methyl group of 6 to 16 carbons is more preferable. It can be exemplified by a methoxymethyl group, a methylthiomethyl group, an ethoxymethyl group, an n-propoxymethyl group, an isopropoxymethyl group, an n-butoxymethyl group, a t-butoxymethyl group, a 2-methylpropoxymethyl group, an ethylthiomethyl group, a methoxyethoxymethyl group, a phenyloxymethyl group, a 1-cyclopentyloxymethyl group, a 1-cyclohexyloxymethyl group, a benzylthiomethyl group, a phenacyl group, a 4-bromophenacyl group, a 4-methoxyphenacyl group, a piperonyl group, substituted groups represented by the following formula (7) and the like.

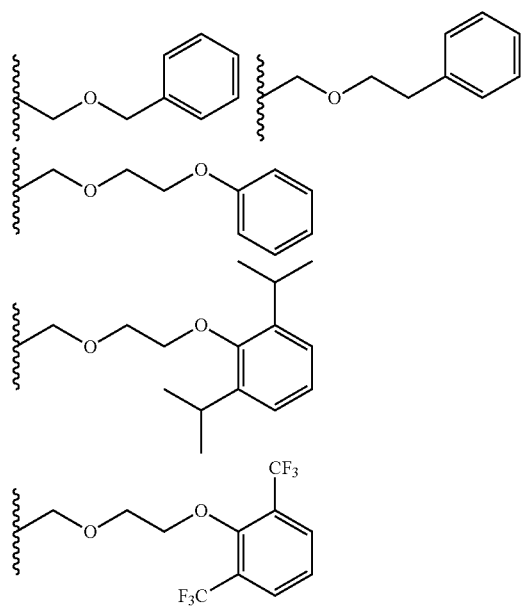

(7)

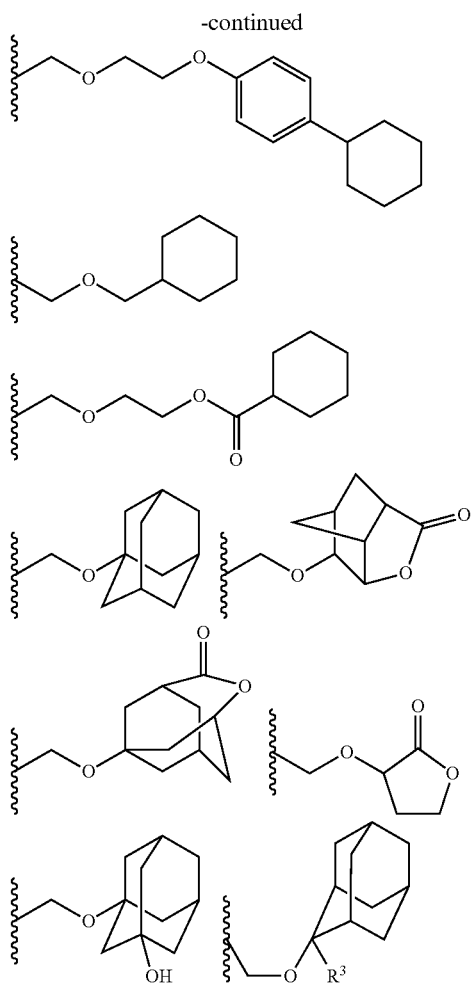

(In the formula (7), $R^3$ is a hydrogen atom or an alkyl group of 1 to 4 carbons. Alkyl groups of 1 to 4 carbons include a methyl group, an ethyl group, an isopropyl group, an n-propyl group, a t-butyl group, an n-butyl group and the like.)

As the 1-substituted ethyl group, a 1-substituted ethyl group of 3 to 20 carbons is normal, a 1-substituted ethyl group of 5 to 18 carbons is preferable, and a substituted ethyl group of 7 to 16 carbons is more preferable. It can be exemplified by a 1-methoxyethyl group, a 1-methylthioethyl group, a 1,1-dimethoxyethyl group, a 1-ethoxyethyl group, a 1-ethylthioethyl group, a 1,1-diethoxyethyl group, an n-propoxyethyl group, an isopropoxyethyl group, an n-butoxyethyl group, a t-butoxyethyl group, a 2-methylpropoxyethyl group, a 1-phenoxyethyl group, a 1-phenylthioethyl group, a 1,1-diphenoxyethyl group, a 1-cyclopentyloxyethyl group, a 1-cyclohexyloxyethyl group, a 1-phenylethyl group, a 1,1-diphenylethyl group, substituted groups represented by the following formula (8) and the like.

(8)

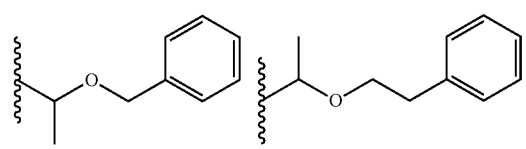

-continued

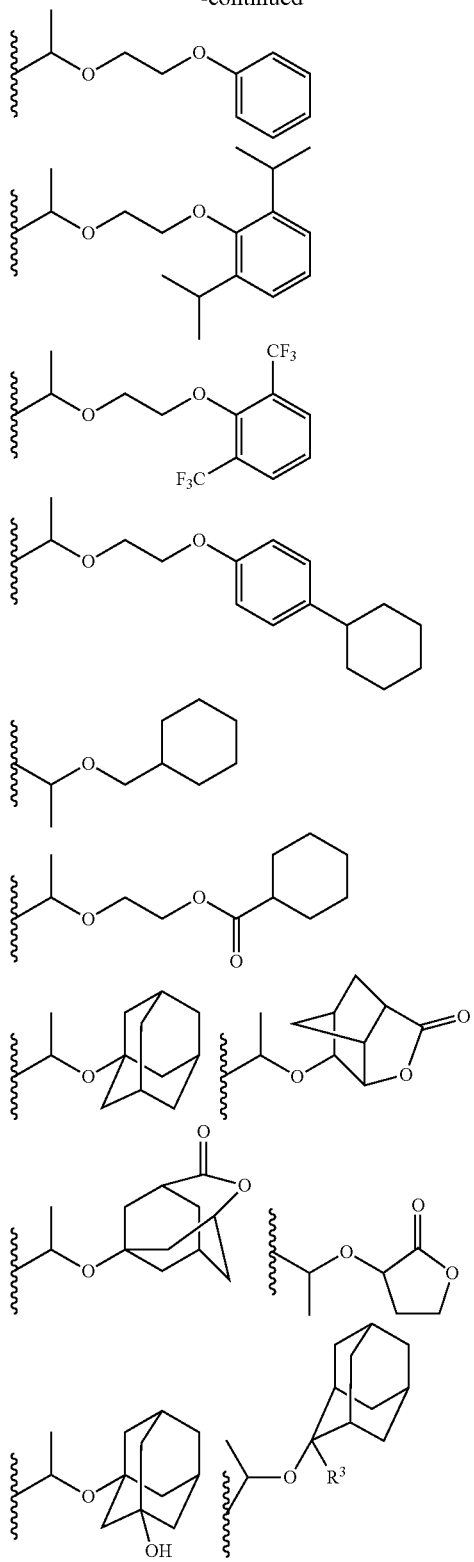

(In the formula (8), R³ is the same as above.)

As the 1-substituted-n-propyl group, a 1-substituted-n-propyl group of 4 to 20 carbons is normal, a 1-substituted-n-propyl group of 6 to 18 carbons is preferable, and a 1-substituted-n-propyl group of 8 to 16 carbons is more preferable. It can be exemplified by a 1-methoxy-n-propyl group, a 1-ethoxy-n-propyl group and the like.

As the 1-branched alkyl group, a 1-branched alkyl group of 3 to 20 carbons is normal, a 1-branched alkyl group of 5 to 18 carbons is preferable, and a branched alkyl group of 7 to 16 carbons is more preferable. It can be exemplified by an isopropyl group, a sec-butyl group, a tert-butyl group, a 1,1-dimethylpropyl group, a 1-methylbutyl group, a 1,1-dimethylbutyl group, a 2-methyladamantyl group, a 2-ethyladamantyl group and the like.

As the silyl group, a silyl group of 1 to 20 carbons is normal, a silyl group of 3 to 18 carbons is preferable, and a silyl group of 5 to 16 carbons is more preferable. It can be exemplified by a trimethylsilyl group, an ethyldimethylsilyl group, a methyldiethylsilyl group, a triethylsilyl group, a tert-butyldimethylsilyl group, a tert-butyldiethylsilyl group, a tert-butyldiphenylsilyl group, a tri-tert-butylsilyl group, a triphenyl group and the like.

As the acyl group, an acyl group of 2 to 20 carbons is normal, an acyl group of 4 to 18 carbons is preferable, and an acyl group of 6 to 16 carbons is more preferable. It can be exemplified by an acetyl group, a phenoxyacetyl group, a propionyl group, a butylyl group, a heptanoyl group, a hexanoyl group, a valeryl group, a pivaloyl group, an isovaleryl group, a lauryloyl group, a adamantylcarbonyl group, a benzoyl group, a naphthoyl group and the like.

As the 1-substituted alkoxyalkyl group, a 1-substituted alkoxyalkyl group of 2 to 20 carbons is normal, a 1-substituted alkoxyalkyl group of 4 to 18 carbons is preferable, and a 1-substituted alkoxyalkyl group of 6 to 16 carbons is more preferable. It can be exemplified by a 1-cyclopentylmethoxymethyl group, a 1-cyclopentylethoxymethyl group, a 1-cyclohexylmethoxymethyl group, a 1-cyclohexylethoxymethyl group, a 1-cyclooctylmethoxymethyl group, a 1-adamantylmethoxymethyl group and the like.

As the cyclic ether group, a cyclic ether group of 2 to 20 carbons is normal, a cyclic ether group of 4 to 18 carbons is preferable, and a cyclic ether group of 6 to 16 carbons is more preferable. It can be exemplified by a tetrahydropyranyl group, a tetrahydrofuranyl group, a tetrahydrothiopyranyl group, a tetrahydrothiofuranyl group, a 4-methoxytetrahydropyranyl group, a 4-methoxytetrahydrothiopyranyl group and the like.

As the alkoxycarbonyl group, an alkoxycarbonyl group of 2 to 20 carbons is normal, an alkoxycarbonyl group of 4 to 18 carbons is preferable, and an alkoxycarbonyl group of 6 to 16 carbons is more preferable. It can be exemplified by a methoxycarbonyl group, an ethoxycarbonyl group, an n-propoxycarbonyl group, an isopropoxycarbonyl group, an n-butoxycarbonyl group, a tert-butoxycarbonyl group, acid dissociable functional groups represented by the following formula (9) wherein n=0, or the like.

As the alkoxycarbonylalkyl group, an alkoxycarbonylalkyl group of 2 to 20 carbons is normal, an alkoxycarbonylalkyl group of 4 to 18 carbons is preferable, and an alkoxycarbonylalkyl group of 6 to 16 carbons is more preferable. It can be exemplified by a methoxycarbonylmethyl group, an ethoxycarbonylmethyl group, an n-propoxycarbonylmethyl group, an isopropoxycarbonylmethyl group, an n-butoxycarbonylmethyl group, acid dissociable functional groups represented by the following formula (9) wherein n=1 to 4, or the like.

(9)

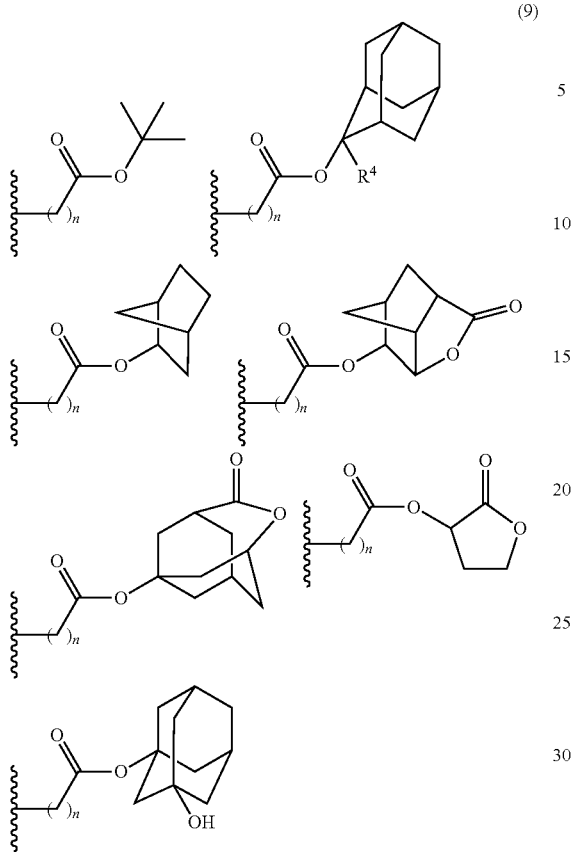

(In the formula (9), $R^4$ is a linear or branched alkyl group of 1 to 4 carbons, and alkyl groups of 1 to 4 carbons include a methyl group, an ethyl group, an isopropyl group, an n-propyl group, a t-butyl group, an n-butyl group and the like. n is an integer of 0 to 4.)

Among these acid dissociable functional groups, a substituted methyl group, a 1-substituted ethyl group, a 1-substituted alkoxyalkyl group, a cyclic ether group, an alkoxycarbonyl group, and an alkoxycarbonylalkyl group are preferable, a substituted methyl group, a 1-substituted ethyl group, an alkoxycarbonyl group and an alkoxycarbonylalkyl group, which are all highly sensitive, are more preferable, and moreover a cycloalkane of 3 to 12 carbons, a lactone and an acid dissociable functional group having a structure selected from 6 to 12 aromatic rings are more preferable. The cycloalkane of 3 to 12 carbons may be monocyclic or polycyclic, but is more preferable to be polycyclic. Specifically, monocycloalkane, bicycloalkane, tricycloalkane, tetracycloalkane and the like are included, more specifically, monocycloalkane such as cyclopropane, cyclobutane, cyclopentane and cyclohexane, and polycycloalkane such as adamantine, norbornane, isobornane, tricyclodecane and tetracyclodecane are included. Among them, adamantine, tricyclodecane and tetracyclodecane are preferable, and adamantine and tricyclodecane are particularly preferable. The cycloalkane of 3 to 12 carbons may have a substituted group. The lactone includes a butyrolactone or a cycloalkane group of 3 to 12 carbons having a lactone group. The 6 to 12 aromatic rings include a benzene ring, a naphthalene ring, an anthracene ring, a phenanthrene ring, a pyrene ring and the like, a benzene ring and a naphthalene ring are preferable, and a naphthalene ring is particularly preferable.

Among the above acid dissociable functional groups, an acid dissociable functional group selected from the group consisting of each group represented by the following formula (10), which has high resolution, is particularly preferable.

(10)

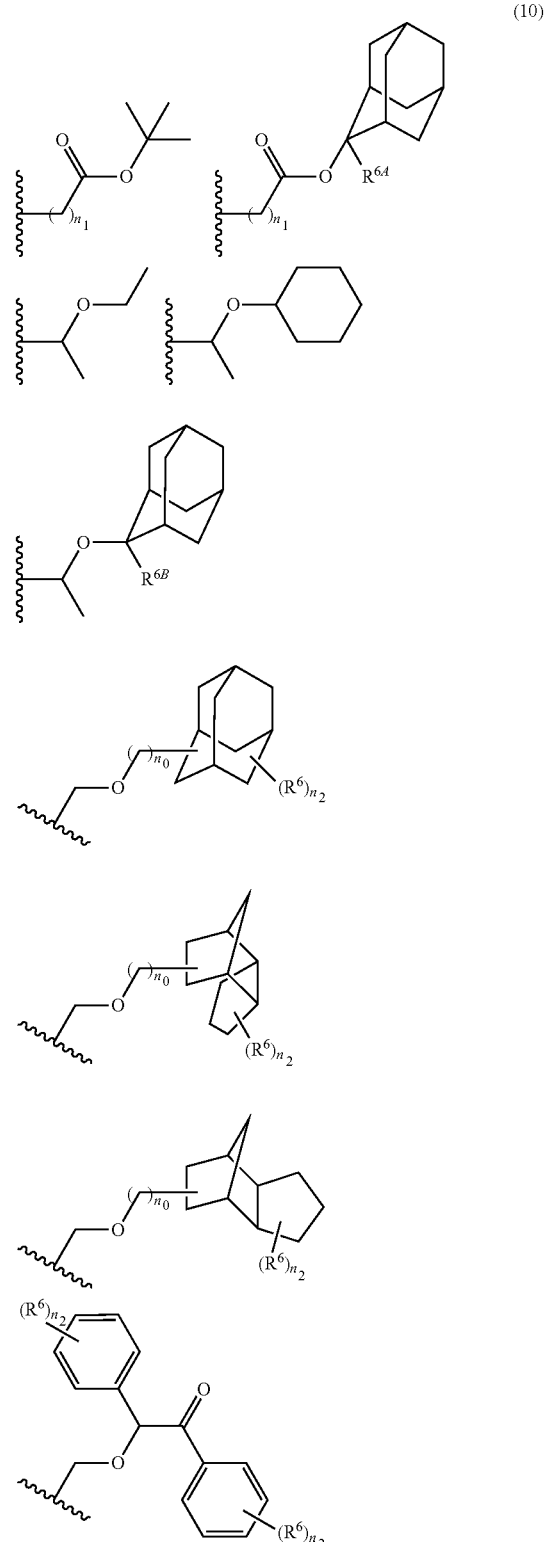

-continued

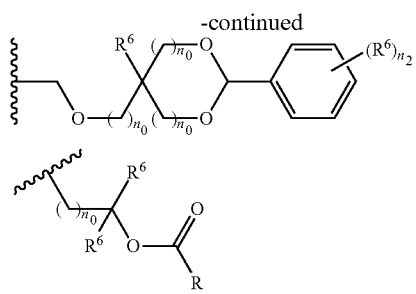

(In the formula (10), $R^{6A}$ is a hydrogen atom, or a linear or branched alkyl group of 1 to 4 carbons, $R^{6B}$ is a linear or branched alkyl group of 1 to 4 carbons, $R^6$ is a hydrogen atom, a linear or branched alkyl group of 1 to 4 carbons, a cyano group, a nitro group, a heterocyclic group, a halogen atom, or a carboxyl group, $n_1$ is an integer of 0 to 4, $n_2$ is an integer of 1 to 5, and $n_0$ is an integer of 0 to 4.)

The compound (B) synthesized by reaction between the polyphenol based cyclic compound (A) represented by the above formula (1) and the compound represented by the above formula (3) becomes, by reacting a phenolic hydroxyl group or carboxyl group of the polyphenol based cyclic compound (A) with an acid crosslinkable reactive group of the compound (C) represented by the above formula (3), an oligomer or a high molecular weight form. For example, it becomes an oligomer form obtained from two molecules of the polyphenol based cyclic compound (A) and two molecules of the compound represented by the above formula (3). Since strength of the resultant resist pattern and adhesion to a base material improve by making a monomer into an oligomer or a high molecular weight form, the problem of pattern collapse seen in a low molecular weight type can be prevented. The molecular weight of the above compound (B) is 1,600 to 50,000, preferably 1,600 to 10,000, and more preferably 1,600 to 5,000. Within the above range, pattern collapse is prevented and resolution is improved while maintaining film formability required for a resist.

Moreover, in the exposed portion, the molecular weight is decreased due to dissociation of an acid dissociable functional group, and roughness of a resist pattern is reduced similarly to a low molecular weight type. Also, it is preferably used as a resist material, particularly a main component (base material) of a resist material, since it has high heat resistance, excellent film formability with amorphousness, no sublimability, excellent alkaline developability, etching resistance and the like.

Furthermore, even from the production aspect, it is extremely excellent in practicability, since it can be produced with a high yield by reacting a polyphenol based cyclic compound (A) obtained by dehydrative condensation reaction of various aldehydes including aromatic aldehyde industrially produced and phenols such as resorcinol, pyrogallol, m-alkoxybenzene and 1,3-dialkoxybenzene or a phenol derivative as raw materials with a non-metal catalyst such as hydrochloric acid, with a compound for introducing di- to tetravalent acid dissociable functional groups easily available as industrial products by a publicly known method.

The cyclic compound (A) represented by the above formula (1) is preferable to include the following compound.

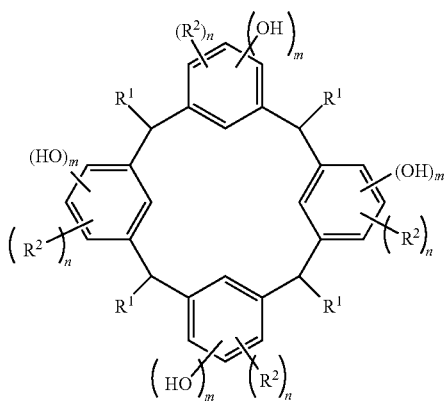

(In the formula (1-1), R, $R^2$, m and n are the same as above.)

The cyclic compound (A) represented by the above formula (1-1) is more preferable to include the following compound.

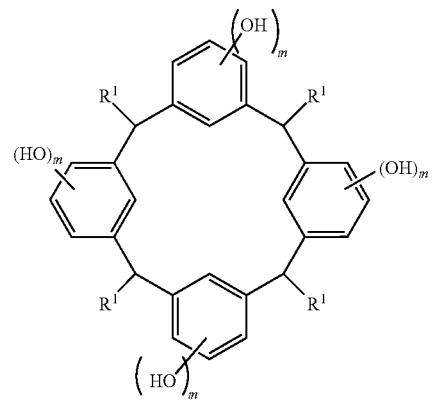

(In the formula (1-2), $R^1$ and m are the same as above.)

The cyclic compound (A) represented by the above formula (1-2) is further preferable to include the following compound.

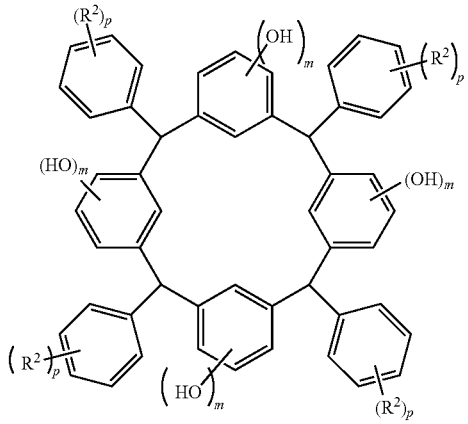

(In the formula (1-3), $R^2$, m and p are the same as above.)

The cyclic compound (A) represented by the above formula (1-3) is particularly preferable to include the following compounds.

(1-4)

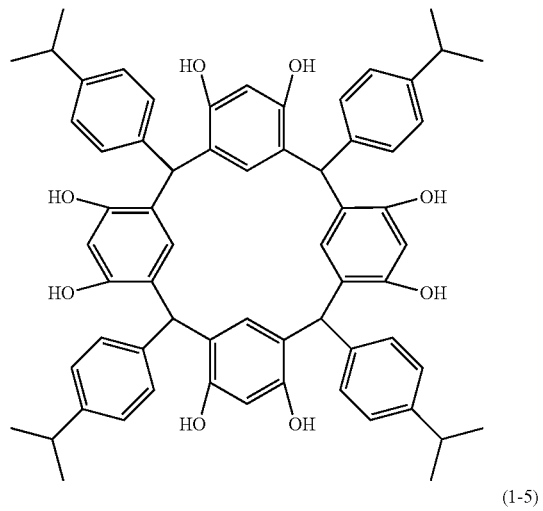

(1-5)

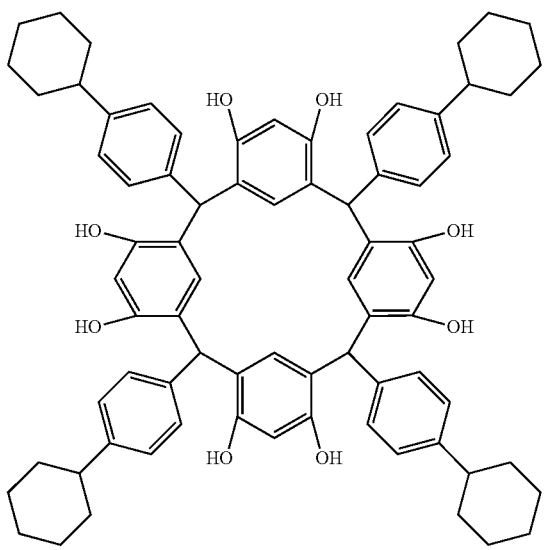

The cyclic compound (A) represented by the above formula (1) is obtained by condensation reaction of one or more kinds selected from the group consisting of carbonyl compounds (A11), and one or more kinds selected from the group consisting of phenols or phenol derivatives (A12).

The carbonyl compounds (A11) include, for example, formaldehyde, acetaldehyde, propionaldehyde, hydroxybenzaldehyde, dihydroxybenzaldehyde, benzaldehyde, methylbenzaldehyde, dimethylbenzaldehyde, ethylbenzaldehyde, propylbenzaldehyde, butylbenzaldehyde, ethylmethylbenzaldehyde, isopropylmethylbenzaldehyde, diethylbenzaldehyde, anisaldehyde, naphthaldehyde, anthraaldehyde, cyclopropylbenzaldehyde, cyclobutanebenzaldehyde, cyclopentanebenzaldehyde, cyclohexanebenzaldehyde, phenylbenzaldehyde, naphthylbenzaldehyde, adamantylbenzaldehyde, norbornylbenzaldehyde, lactylbenzaldehyde, isopropylbenzaldehyde, normalpropylbenzaldehyde, bromobenzaldehyde, dimethylaminobenzaldehyde, cyclopropylbenzaldehyde, cyclobutanebenzaldehyde, cyclopentanebenzaldehyde, cyclohexanebenzaldehyde, phenylbenzaldehyde, naphthylbenzaldehyde, adamantylbenzaldehyde, norbornylbenzaldehyde, lactylbenzaldehyde, hydroxybenzaldehyde, dihydroxybenzaldehyde and the like, propylbenzaldehyde, butylbenzaldehyde, hydroxybenzaldehyde, cyclohexylbenzaldehyde and phenylbenzaldehyde are preferable, propylbenzaldehyde, butylbenzaldehyde, cyclohexylbenzaldehyde and phenylbenzaldehyde are more preferable, and propylbenzaldehyde and cyclohexylbenzaldehyde are further preferable.

The carbonyl compounds (A11) may have a linear or branched alkyl group of 1 to 4 carbons, a cyano group, a hydroxyl group, a halogen atom and the like within the range of not deteriorating the effect of the invention. The carbonyl compounds (A11) may be used alone or in combination of two or more kinds, but it is more preferable to use two or more kinds of the aromatic carbonyl compounds (A11). By using two or more kinds of the aromatic carbonyl compounds (A11), dissolvability of the resultant cyclic compound in a semiconductor safe solvent improves.

The phenols and/or phenol derivatives (A12) include phenol, catechol, resorcinol, hydroquinone, pyrogallol, m-alkoxyphenol, 1,3-dialkoxybenzene and the like, which may have a substituted group to be describe below, m-alkoxyphenol, 1,3-dialkoxybenzene, resorcinol and pyrogallol are preferable, m-methoxyphenol, 1,3-dimethoxybenzene, resorcinol and pyrogallol are more preferable, resorcinol and pyrogallol are further preferable, and resorcinol is preferably preferable. The phenols and/or phenol derivatives (A12) may have a linear or branched alkyl group of 1 to 20 carbons, a cyclic alkyl group of 1 to 20 carbons, an aryl group of 6 to 20 carbons, a cyano group, a hydroxyl group, a halogen atom and the like, within the range of not deteriorating the effect of the invention. The phenols and/or phenol derivatives (A12) may be used alone or in combination of two or more kinds.

The cyclic compound (A) represented by the above formula (1) can be produced by a publicly known method. For example, it is obtained by reacting 0.1 to 10 moles of the phenols and/or phenol derivatives (A12) based on 1 mole of the carbonyl compounds (A11) at 60 to 150° C. for about 0.5 to 20 hours in an organic solvent such as methanol or ethanol using an acid catalyst (such as hydrochloric acid, sulfuric acid or para-toluene sulfonic acid), filtering, washing with alcohols such as methanol, washing with water, filtering, and drying. It is also obtained by using a basic catalyst (such as sodium hydroxide, barium hydroxide or 1,8-diazabicyclo[5.4.0]undecene-7) instead of the acid catalyst, and reacting in the same way. Moreover, the compound represented by the above formula (1) can also be produced by treating the above carbonyl compounds (A11) with hydrogen halide or halogen gas into dihalide, and reacting the isolated dihalide with the phenols and/or phenol derivatives (A12).

The compound (C) represented by the above formula (3) is preferable to include the following compounds.

(3-1)

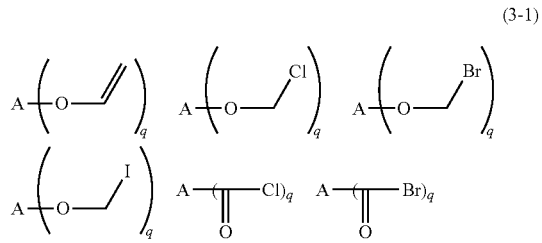

-continued

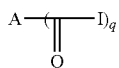

In the above formula (3-1), A is an aliphatic hydrocarbon group of 1 to 18 carbons, a alicyclic hydrocarbon group of 3 to 18 carbons or an aromatic hydrocarbon group of 6 to 24 carbons, and q is an integer of 2 to 4.

The aliphatic hydrocarbon group of 1 to 18 carbons includes di- to tetravalent groups having methane, ethane, propane, butane, pentane, hexane, heptane, octane, decane, dodecane or undecane.

The alicyclic hydrocarbon group of 3 to 18 carbons includes di- to tetravalent groups having a cyclopentane ring, a cyclobutane ring, a cyclohexane ring, an adamantine ring, a dicyclopentane ring or a tricyclodecane ring, di- or tetravalent groups having a cyclohexane ring, an adamantine ring, a dicyclopentane ring or a tricyclodecane ring are preferable, and a cyclohexane ring or an adamantine ring are further preferable.

The aromatic hydrocarbon group of 6 to 24 carbons includes di- to tetravalent groups having a benzene ring, a naphthalene ring, a phenanthrene ring, an anthracene ring or a pyrene ring, divalent to tetravalent groups having a benzene ring or a naphthalene ring are preferable, and divalent to tetravalent groups having a benzene ring are more preferable.

The compounds represented by the above formula (3-1) are more preferable to include the following compounds.

(3-2)

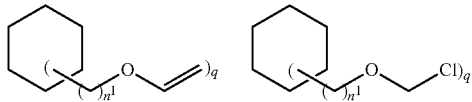
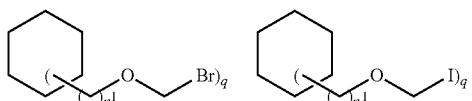
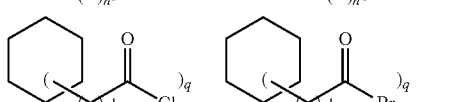
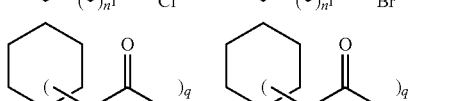
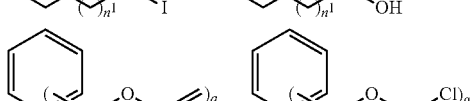
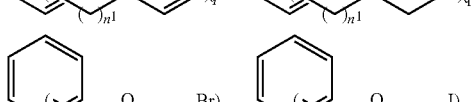
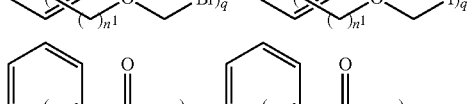
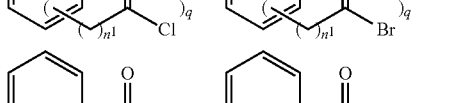

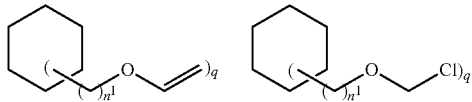
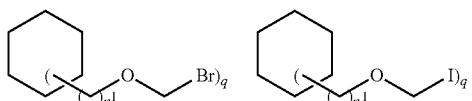
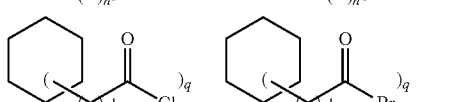
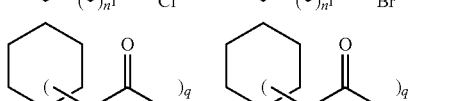
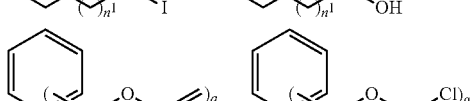
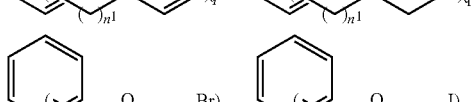
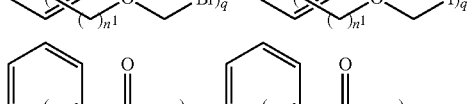
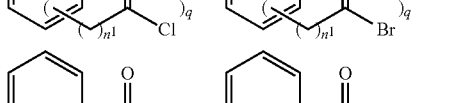

(In the formula (3-2), $n_1$ is an integer of 0 to 2, and q is an integer of 2 to 4.)

The compounds represented by the above formula (3-2) are further preferable to include the following compounds.

(3-3)

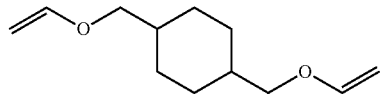
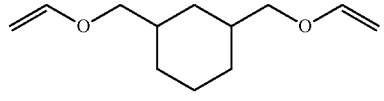
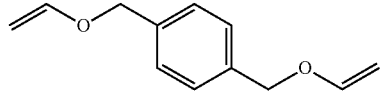
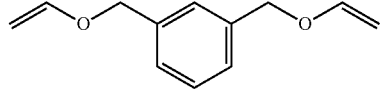

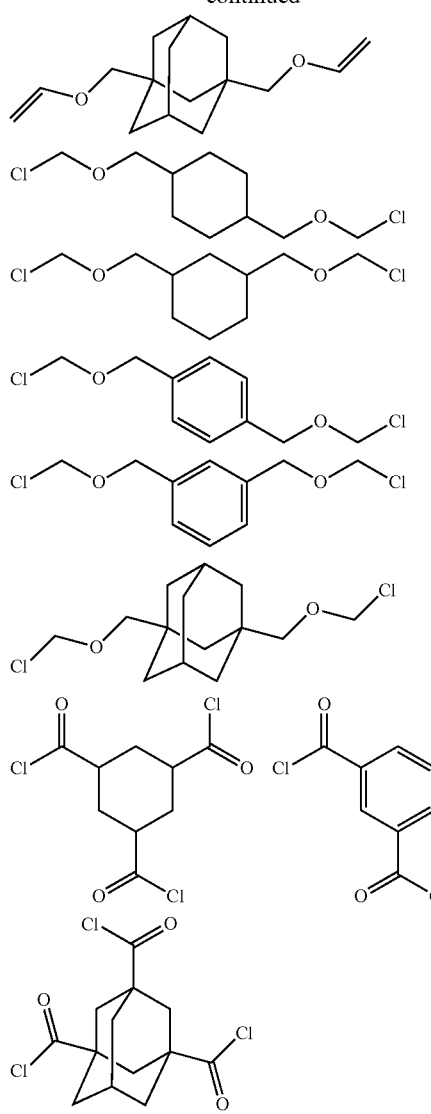
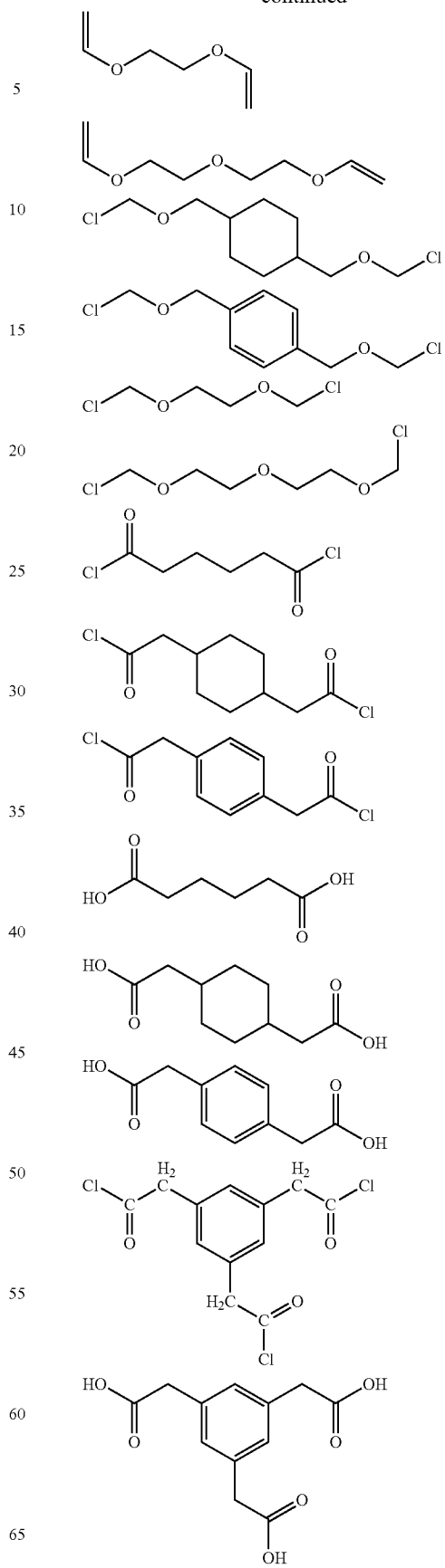
The compound (C) represented by the above formula (3) can be synthesized by a publicly known method or easily obtained, and is exemplified by, but not particularly limited to, the compounds represented by the following formula (3-4).
(3-4)
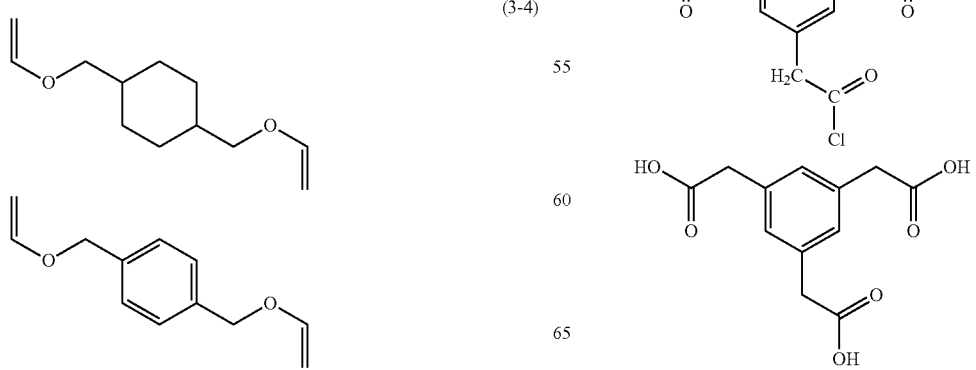

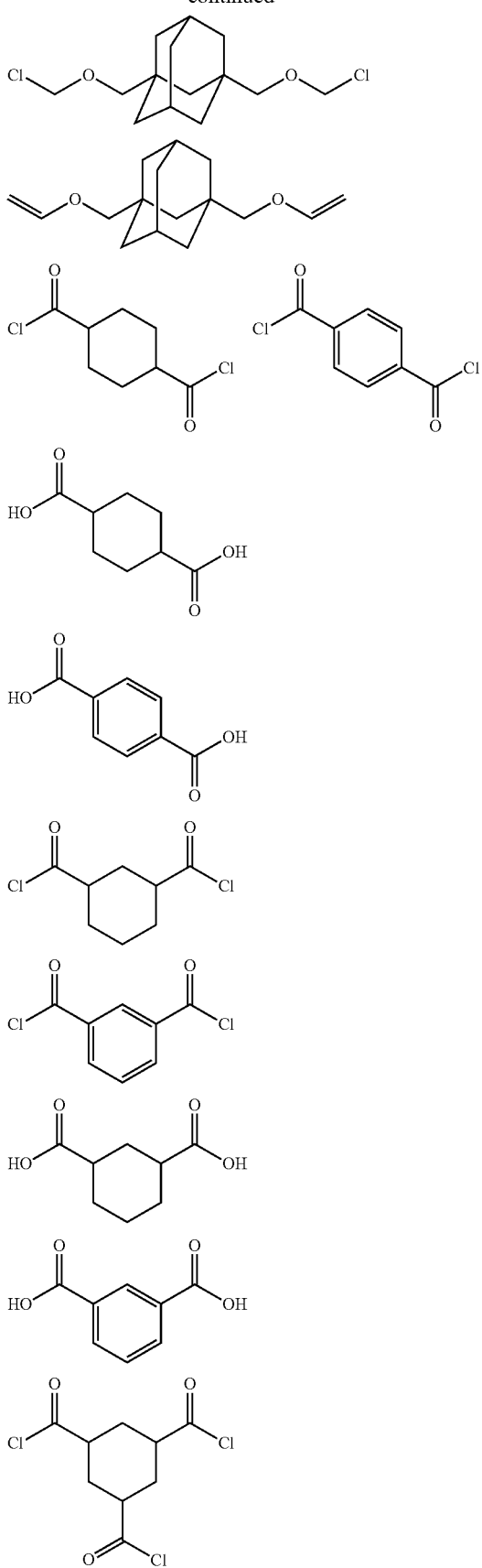

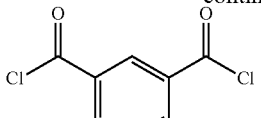

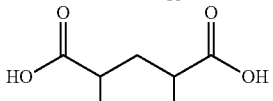

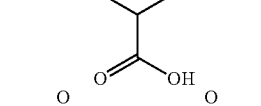

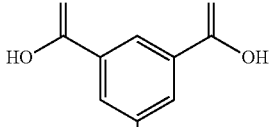

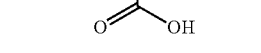

The compound (B) is obtained by reacting at least one phenolic hydroxyl group or carboxyl group of the cyclic compound (A) with the compound (C) by a publicly known method. For example, at least one phenolic hydroxyl group or carboxyl group of the compound (A) can be reacted with the compound (C) as follows.

For example, the compound (A) is dissolved or suspended in an aprotic solvent such as acetone, tetrahydrofuran (THF), and propylene glycol monomethyl ether acetate. Next, divinylalkylether such as divinyloxymethylcyclohexane is added, and it is reacted in the presence of an acid catalyst such as trifluoroacetic acid and pyridinium p-toluenesulfonate, at normal pressure, at 20 to 60° C., for 6 to 72 hours. The compound (B) can be obtained by neutralizing the reaction solution with an alkaline compound, adding it to distilled water to precipitate a white solid, then washing the isolated white solid with distilled water, and drying.

Moreover, the compound (A) is dissolved or suspended in an aprotic solvent such as acetone, THF and propylene glycol monomethyl ether acetate. Next, benzenetricarboxylic acid chloride is added, and it is reacted in the presence of an alkaline catalyst such as potassium carbonate, at normal pressure, at 20 to 110° C., for 6 to 72 hours. The compound (B) can be obtained by neutralizing the reaction solution with acid such as hydrochloric acid, adding it to distilled water to precipitate a white solid, then washing the isolated white solid with distilled water, and drying.

In order to reduce the amount of remaining metal in the compound (B), it may be purified if necessary. Since storage stability of a positive type radiation-sensitive composition generally decreases when an acid catalyst remains, or sensitivity of a positive type radiation-sensitive composition generally decreases when a basic catalyst remains, purification may be conducted with a view to reducing the same. Purification can be conducted by a publicly known method unless the compound (B) is modified, and is exemplified by, but not particularly limited to a method of washing with water, a method of washing with an acidic aqueous solution, a method of washing with a basic aqueous solution, a method of treating with an ion exchange resin, a method of treating with silica gel column chromatography and the like.

It is more preferable to conduct these purification methods in combination of two or more kinds. It is possible to arbitrarily select the optimal one for acidic aqueous solution, basic aqueous solution, ion exchange resin and silica gel column chromatography, according to the amount and the kind of metal, acidic compound and/or basic compound to be removed, the kind of dissolution inhibitor to be purified, and the like. For example, acidic aqueous solutions include aqueous solutions of hydrochloric acid, nitric acid and acetic acid with a concentration of 0.01 to 10 mol/L, basic aqueous solutions include an ammonia aqueous solution with a concentration of 0.01 to 10 mol/L, and ion exchange resins include a cation exchange resin, for example Amberlyst 15J-HG Dry manufactured by Organo.

Moreover, drying may be conducted after purification. Drying can be conducted by a publicly known method, and is exemplified by, but not particularly limited to, methods of vacuum drying, hot air drying, and the like under the condition where the compound (B) is not modified.

The compound (A) as a raw material of the compound (B) of the invention may be in the cis form or the trans form, but may be any structure or mixture. When a positive type radiation-sensitive composition is used as a resist component, it is preferable to have a structure of either the cis form or the trans form only, since uniformity of components in a resist film is high. A method for obtaining the compound (A) having a structure of either the cis form or the trans form only can be conducted by a publicly known method such as separation with column chromatography or preparative liquid chromatography, optimization of reaction solvent, reaction temperature and the like upon production, and the like.

The glass transition temperature of the compound (B) of the invention is preferably not less than 100° C., more preferably not less than 120° C., further preferably not less than 140° C., and particularly preferably not less than 150° C. By having the glass transition temperature within the above range, in the semiconductor lithography process, it can have heat resistance capable of maintaining a pattern shape, and impart performance such as high resolution.

The crystallization heat generation amount obtained by differential scanning calorimetrical analysis of the glass transition temperature of the compound (B) of the invention is preferably less than 20 J/g. Also, (crystallization temperature)–(glass transition temperature) is preferably not less than 70° C., more preferably not less than 80° C., further preferably not less than 100° C., and particularly preferably not less than 130° C. When the crystallization heat generation amount is less than 20 J/g or (crystallization temperature)–(glass transition temperature) is within the above range, by spin coating a positive type radiation-sensitive composition, an amorphous film is easy to be formed, film formability required for a resist can be retained over an extended period of time, and resolution can be improved.

In the invention, the above crystallization heat generation amount, crystallization temperature and glass transition temperature can be measured as below by using DSC/TA-SOWS manufactured by Shimadzu and obtained by differential scanning calorimetrical analysis. About 10 mg of a sample is placed in a non-sealed container made of aluminum, and the temperature is raised to the melting point or above at a temperature rise rate of 20° C./min in a nitrogen gas stream (50 ml/min) After rapid cooling, again the temperature is raised to the melting point or above at a temperature rise rate of 20° C./min in a nitrogen gas stream (30 ml/min) After further rapid cooling, again the temperature is raised to 400° C. at a temperature rise rate of 20° C./min in a nitrogen gas stream (30 ml/min). The temperature at the middle point of the region where the discontinuous portion appears in the baseline (where the specific heat is changed to half) is the glass transition temperature (Tg), and the temperature at the subsequently appearing heat generation peak is the crystallization temperature. The heat generation amount is obtained from the area of the region surrounded by the heat generation peak and the baseline, as the crystallization heat generation amount.

The compound (B) is preferable to have low sublimability under normal pressure at not more than 100° C., preferably not more than 120° C., more preferably not more than 130° C., further preferably not more than 140° C. and particularly preferably not more than 150° C. Here, low sublimability means that in thermogravimetrical analysis, the weight reduction upon being kept at a predetermined temperature for 10 minutes is not more than 10%, preferably 5%, more preferably 3%, further preferably 1%, and particularly preferably 0.1%. By having low sublimability, contamination of an exposure equipment by outgas upon exposure can be prevented. Also, a good pattern shape can be provided with low LER.

The compound (B) meets preferably F<3.0 (F represents total atom number/(total carbon atom number−total oxygen atom number)), and more preferably F<2.5. By meeting the above condition, it becomes excellent in dry etching resistance.

The compound (B) dissolves in a solvent selected from propylene glycol monomethyl ether acetate (PGMEA), propylene glycol monomethyl ether (PGME), cyclohexanone (CHN), cyclopentanone (CPN), 2-heptanone, anisole, butyl acetate, ethyl propionate and ethyl lactate, and showing the highest dissolvability to the compound (B), in preferably not less than 1% by weight, more preferably not less than 5% by weight, and further preferably not less than 10% by weight at 23° C., and particularly preferably in a solvent selected from PGMEA, PGME and CHN, and showing the highest dissolvability to the compound (B), in not less than 20% by weight at 23° C. By meeting the above condition, the use in the semiconductor production process in the actual production becomes possible, and storage stability also becomes good.

Within the range of not deteriorating the effect of the invention, a non-acid dissociable functional group may be introduced into at least one phenolic hydroxyl group and/or carboxyl group of the compound (B). The non-acid dissociable functional group refers to a characteristic group not cleaving in the presence of acid or not generating an alkali soluble group. It is exemplified by functional groups selected from the group consisting of a C1 to 20 alkyl group, a C3 to 20 cycloalkyl group, a C6 to 20 aryl group, a C1 to 20 alkoxyl group, a cyano group, a nitro group, a hydroxyl group, a heterocyclic group, a halogen atom, a carboxyl group, a C1 to 20 alkylsilyl group and derivatives thereof, which are not degraded by action of acid, and the like.

[Positive Type Radiation-Sensitive Composition]

By using the compound (B) of the invention, an amorphous film can be formed by spin coating. Also, it can be used in a typical semiconductor production process.

The positive type radiation-sensitive composition of the invention comprises the above compound (B), an acid generator (D) generating acid directly or indirectly by irradiation of any radiation selected from the group consisting of visible light, ultraviolet light, excimer laser, electron beam, extreme ultraviolet light (EUV), X-ray and ion beam, an acid diffusion controller (E), and a solvent.

By using this positive type radiation-sensitive composition, collapse of the resultant resist pattern can be prevented, and also roughness of the resist pattern can be reduced.

Moreover, the positive type radiation-sensitive composition of the invention can form an amorphous film by spin coating. The dissolution rate of the amorphous film formed by spin coating the positive type radiation-sensitive compound of the invention in a 2.38% by mass TMAH aqueous solution at 23° C. is preferably not less than 5 Å/sec, more preferably 0.05 to 5 Å/sec, and further preferably 0.0005 to 5 Å/sec. With not more than 5 Å/sec, it is insoluble in an alkaline developing solution, and can be a resist. Also, when it has the dissolution rate of not less than 0.0005 Å/sec, resolution may improve. It is presumed that this is because due to the change in dissolvability before and after exposure of a cyclic compound, contrast at the interface between the unexposed portion dissolved in an alkaline developing solution and the exposed portion not dissolved in an alkaline developing solution becomes large. In addition, there are effects of reducing LER and defect.

Furthermore, the dissolution rate of the portion of the amorphous film formed by spin coating a solid component of the positive type radiation-sensitive composition of the invention exposed by radiation such as KrF excimer laser, extreme ultraviolet light, electron beam or X-ray in a 2.38% by mass TMAH aqueous solution at 23° C. is preferably not less than 10 Å/sec, more preferably 10 to 10,000 Å/sec, and further preferably 100 to 1,000 Å/sec. With not less than 10 Å/sec, it dissolves in an alkaline developing solution, and can be a resist. Also, when it has the dissolution rate of not more than 10,000 Å/sec, resolution may improve. It is presumed that this is because the micro surface portion of the cyclic compound dissolves and reduces LER. In addition, there is an effect of reducing defect.

Moreover, the positive type radiation-sensitive composition comprises 1 to 80% by weight of solid component and 20 to 99% by weight of solvent. It comprises preferably 1 to 50% by weight of solid component and 50 to 99% by weight of solvent, further preferably 2 to 40% by weight of solid component and 60 to 98% by weight of solvent, and particularly preferably 2 to 10% by weight of solid component and 90 to 98% by weight of solvent.

Furthermore, the amount of the compound (B) is 50 to 99% by weight, preferably 65 to 80% by weight, and more preferably 60 to 70% by weight of the total weight of solid component. With the above compounding percentages, high resolution is obtained and line edge roughness becomes small.

Here, the above acid generator (D) is preferable to be at least one kind selected from the group consisting of compounds represented by the following formulae (7-1) to (7-8).

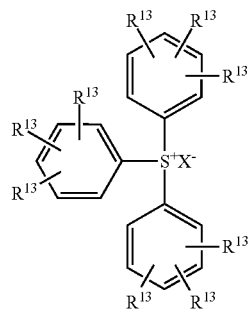

(7-1)

(In the formula (7-1), $R^{13}$ may be the same or different, and are each independently a hydrogen atom, a linear, branched or cyclic alkyl group, a linear, branched or cyclic alkoxy group, a hydroxyl group or a halogen atom; $X^-$ is a sulfonic acid ion having an alkyl group, an aryl group, a halogen substituted alkyl group or a halogen substituted aryl group, or a halide ion.)

The compound represented by the above formula (7-1) is preferable to be at least one kind selected from the group consisting of triphenylsulfonium trifluoromethanesulfonate, triphenylsulfonium nonafluoro-n-butanesulfonate, diphenyltolylsulfonium nonafluoro-n-butanesulfonate, triphenylsulfonium perfluoro-n-octanesulfonate, dipheny-4-methylphenylsulfonium trifluoromethanesulfonate, di-2,4,6-trimethylphenylsulfonium trifluoromethanesulfonate, diphenyl-4-t-butoxyphenylsulfonium trifluoromethanesulfonate, diphenyl-4-t-butoxyphenylsulfonium nonafluoro-n-butanesulfonate, diphenyl-4-hydroxyphenylsulfonium trifluoromethanesulfonate, bis(4-fluorophenyl)-4-hydroxyphenylsulfonium trifluoromethanesulfonate, diphenyl-4-hydroxyphenylsulfonium nonafluoro-n-butanesulfonate, bis(4-hydroxyphenyl)-phenylsulfonium trifluoromethanesulfonate, tri(4-methoxyphenyl)sulfonium trifluoromethanesulfonate, tri(4-fluorophenyl)sulfonium trifluoromethanesulfonate, triphenylsulfonium p-toluenesulfonate, triphenylsulfonium benzenesulfonate, diphenyl-2,4,6-trimethylphenyl-p-toluenesulfonate, diphenyl-2,4,6-trimethylphenylsulfonium-2-trifluoromethylbenzenesulfonate, diphenyl-2,4,6-trimethylphenylsulfonium-4-trifluoromethylbenzenesulfonate, diphenyl-2,4,6-trimethylphenylsulfonium-2,4-difluorobenzenesulfonate, diphenyl-2,4,6-trimethylphenylsulfonium hexafluorobenzenesulfonate, diphenylnaphthylsulfonium trifluoromethanesulfonate, diphenyl-4-hydroxyphenylsulfonium-p-toluenesulfonate, triphenylsulfonium 10-camphersulfonate, diphenyl-4-hydroxyphenylsulfonium 10-camphersulfonate and cyclo(1,3-perfluoropropanedisulfone)imidate.

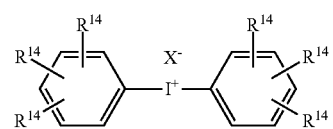

(7-2)

(In the formula (7-2), $R^{14}$ may be the same or different, and each independently represents a hydrogen atom, a linear, branched or cyclic alkyl group, a linear, branched or cyclic alkoxy group, a hydroxyl group or a halogen atom. $X^-$ is the same as above.)

The compound represented by the above formula (7-2) is preferable to be at least one kind selected from the group consisting of bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium p-toluenesulfonate, bis(4-t-butylphenyl)iodonium benzenesulfonate, bis(4-t-butylphenyl)iodonium-2-trifluoromethylbenzenesulfonate, bis(4-t-butylphenyl)iodonium-4-trifluoromethylbenzenesulfonate, bis(4-t-butylphenyl)iodonium-2,4-difluorobenzenesulfonate, bis(4-t-butylphenyl)iodonium hexafluorobenzenesulfonate, bis(4-t-butylphenyl)iodonium 10-camphersulfonate, diphenyliodonium trifluoromethanesulfonate, diphenyliodonium nonafluoro-n-butanesulfonate, diphenyliodonium perfluoro-n-octanesulfonate, diphenyliodonium p-toluenesulfonate, diphenyliodonium benzenesulfonate, diphenyliodonium 10-camphersulfonate, diphenyliodonium-2-trifluoromethylbenzenesulfonate, diphenyliodonium-4-trifluoromethylbenzenesulfonate, diphenyliodonium-2,4-difluorobenzenesulfonate, diphenyliodonium hexafluorobenzenesulfonate, di(4-trifluoromethylphenyl)iodonium trifluoromethanesulfonate, di(4-trifluoromethylphenyl)iodonium nonafluoro-n-butanesulfonate, di(4-trifluoromethylphenyl)iodonium perfluoro-n-octanesulfonate, di(4-trifluoromethylphenyl)iodonium p-toluenesulfonate, di(4-trifluoromethylphenyl)iodonium benzenesulfonate and di(4-trifluoromethylphenyl)iodonium 10-camphersulfonate.

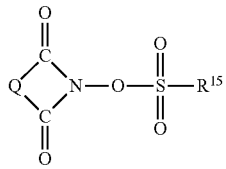

(7-3)

(In the formula (7-3), Q is an alkylene group, an arylene group or an alkoxylene group, and $R^{15}$ is an alkyl group, an aryl group, a halogen substituted alkyl group or a halogen substituted aryl group.)

The compound represented by the above formula (7-3) is preferable to be at least one kind selected from the group consisting of N-(trifluoromethylsulfonyloxy)succinimide, N-(trifluoromethylsulfonyloxy)phthalimide, N-(trifluoromethylsulfonyloxy)diphenylmaleimide, N-(trifluoromethylsulfonyloxy)bicyclo[2.2.1]hept-5-ene-2,3-dicarboxylmide, N-(trifluoromethylsulfonyloxy)naphthylimide, N-(10-camphersulfonyloxy)succinimide, N-(10-camphersulfonyloxy)phthalimide, N-(10-camphersulfonyloxy)diphenylmaleimide, N-(10-camphersulfonyloxy)bicyclo[2.2.1]hept-5-ene-2,3-dicarboxylmide, N-(10-camphersulfonyloxy)naphthylimide, N-(n-octanesulfonyloxy)bicyclo[2.2.1]hept-5-ene-2,3-dicarboxylmide, N-(n-octanesulfonyloxy)naphthylimide, N-(p-toluenesulfonyloxy)bicyclo[2.2.1]hept-5-ene-2,3-dicarboxyimide, N-(p-toluenesulfonyloxy)naphthylimide, N-(2-trifluoromethylbenzenesulfonyloxy)bicyclo[2.2.1]hept-5-ene-2,3-dicarboxylmide, N-(2-trifluoromethylbenzenesulfonyloxy)naphthylimide, N-(4-trifluoromethylbenzenesulfonyloxy)bicyclo[2.2.1]hept-5-ene-2,3-dicarboxylmide, N-(4-trifluorobenzenesulfonyloxy)naphthylimide, N-(perfluorobenzenesulfonyloxy)bicyclo[2.2.1]hept-5-ene-2,3-dicarboxylmide, N-(perfluorobenzenesulfonyloxy)naphthylimide, N-(1-naphthalenesulfonyloxy)bicyclo[2.2.1]hept-5-ene-2,3-dicarboxylmide, N-(1-naphthalenesulfonyloxy)naphthylimide, N-(nonafluoro-n-butanesulfonyloxy)bicyclo [2.2.1] hept-5-ene-2,3-dicarboxylmide, N-(nonafluoro-n-butanesulfonyloxy)naphthylimide, N-(perfluoro-n-octanesulfonyloxy)bicyclo[2 2.1]hept-5-ene-2,3-dicarboxylmide and N-(perfluoro-n-octanesulfonyloxy)naphthylimide.

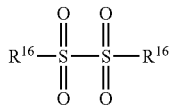

(7-4)

(In the formula (7-4), $R^{16}$ may be the same or different, and are each independently an optionally substituted linear, branched or cyclic alkyl group, an optionally substituted aryl group, an optionally substituted heteroaryl group or an optionally substituted aralkyl group.)

The compound represented by the above formula (7-4) is preferable to be at least one kind selected from the group consisting of diphenyldisulfone, di(4-methylphenyl)disulfone, dinaphthyldisulfone, di(4-tert-butylphenyl)disulfone, di(4-hydroxyphenyl)disulfone, di(3-hydroxynaphthyl)disulfone, di(4-fluorophenyl)disulfone, di(2-fluorophenyl)disulfone and di(4-trifluoromethylphenyl)disulfone.

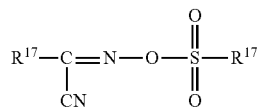

(7-5)

(In the formula (7-5), $R^{17}$ may be the same or different, and are each independently an optionally substituted linear, branched or cyclic alkyl group, an optionally substituted aryl group, an optionally substituted heteroaryl group or an optionally substituted aralkyl group.)

The compound represented by the above formula (7-5) is preferable to be at least one kind selected from the group consisting of α-(methylsulfonyloxyimino)-phenylacetonitrile, α-(methylsulfonyloxyimino)-4-methoxyphenylacetonitrile, α-(trifluoromethylsulfonyloxyimino)-phenylacetonitrile, α-(trifluoromethylsulfonyloxyimino)-4-methoxyphenylacetonitrile, α-(ethylsulfonyloxyimino)-4-methoxyphenylacetonitrile, α-(propylsulfonyloxyimino)-4-methylphenylacetonitrile and α-(methylsulfonyloxyimino)-4-bromophenylacetonitrile.

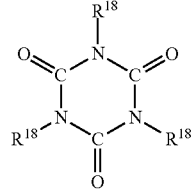

(7-6)

(In the formula (7-6), $R^{18}$ may be the same or different, and are each independently an alkyl halide group having one or more chlorine atoms and one or more bromine atoms. The number of carbon atoms of the alkyl halide group is preferably 1 to 5.)

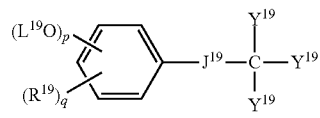

(7-7)

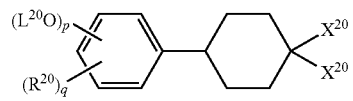

(7-8)

(In the formulae (7-7) and (7-8), $R^{19}$ and $R^{20}$ are each independently an alkyl group of 1 to 3 carbon atoms such as a methyl group, an ethyl group, an n-propyl group and an isopropyl group, a cycloalkyl group such as a cyclopentyl group and a cyclohexyl group, an alkoxyl group of 1 to 3 carbon atoms such as a methoxy group, an ethoxy group and a propoxy group, or aryl group such as a phenyl group, a toluoyl group and a naphthyl group, and preferably an aryl group of 6 to 10 carbon atoms. $L^{19}$ and $L^{20}$ are each independently an organic group having a 1,2-naphthoquinoneazide group.)

The organic group having a 1,2-naphthoquinoneazide group can specifically be exemplified by a 1,2-quinonediazidesulfonyl group such as a 1,2-naphthoquinonediazide-4-sulfonyl group, a 1,2-naphthoquinonediazide-5-sulfonyl group and a 1,2-naphthoquinonediazide-6-sulfonyl group. Particularly, a 1,2-naphthoquinonediazide-4-sulfonyl group and a 1,2-naphthoquinonediazide-5-sulfonyl group are preferable. p is an integer of 1 to 3, q is an integer of 0 to 4, and $1 \le p+q \le 5$. $J^{19}$ is a single bond, a polymethylene group of 1 to 4 carbon atoms, a cycloalkylene group, a phenylene group, a group represented by the following formula (7-7-1), a carbonyl group, an ester group, an amide group or an ether group, $Y^{19}$ is a hydrogen atom, an alkyl group or an aryl group, and $X^{20}$ are each independently a group represented by the following formula (7-8-1).

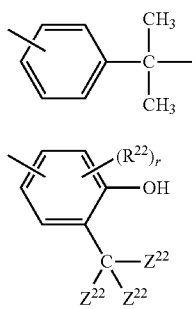

(7-7-1)

(7-8-1)

(In the formula (7-8-1), $Z^{22}$ are each independently an alkyl group, a cycloalkyl group or an aryl group, $R^{22}$ is an alkyl group, a cycloalkyl group or an alkoxyl group, and r is an integer of 0 to 3.)

The other acid generators include bissulfonyldiazomethanes such as bis(p-toluenesulfonyl)diazomethane, bis(2,4-dimethylphenylsulfonyl)diazomethane, bis(tert-butylsulfonyl)diazomethane, bis(n-butylsulfonyl)diazomethane, bis(isobutylsulfonyl)diazomethane, bis(isopropylsulfonyl)diazomethane, bis(n-propylsulfonyl)diazomethane, bis(cyclohexylsulfonyl)diazomethane, bis(isopropylsulfonyl)diazomethane, 1,3-bis(cyclohexylsulfonylazomethylsulfonyl)propane, 1,4-bis(phenylsulfonylazomethylsulfonyl)butane, 1,6-bis(phenylsulfonylazomethylsulfonyl)hexane and 1,10-bis(cyclohexylsulfonylazomethylsulfonyl)decane, halogen-containing triazine derivatives such as 2-(4-methoxyphenyl)-4,6-(bistrichloromethyl)-1,3,5-triazine, 2-(4-methoxynaphthyl)-4,6-(bistrichloromethyl)-1,3,5-triazine, tris(2,3-dibromopropyl)-1,3,5-triazine and tris(2,3-dibromopropyl)isocyanurate, and the like.

Among the above acid generators, an acid generator having an aromatic ring is preferable, and an acid generator represented by the formula (7-1) or (7-2) is more preferable. An acid generator represented by the formula (7-1) or (7-2) wherein $X^-$ is a sulfonic acid ion having an aryl group or a halogen-substituted aryl group is further preferable, an acid generator having a sulfonic acid ion having an aryl group is particularly preferable, and diphenyltrimethylphenylsulfonium p-toluenesulfonate, triphenylsulfonium p-toluenesulfonate, triphenylsulfonium trifluoromethanesulfonate and triphenylsulfonium nonafluoromethanesulfonate are particularly preferable. By using the acid generator, LER can be reduced.

In addition, the above acid generator (D) can be used alone or in combination of two or more kinds.

The positive type radiation-sensitive composition of the invention comprises an acid diffusion controller (E) having a function of controlling diffusion of acid generated from an acid generator by radiation irradiation in a resist film to inhibit any unpreferable chemical reaction in the unexposed region. By comprising such an acid diffusion controller (E), storage stability of the positive type radiation-sensitive composition improves. Also, along with improvement of resolution, the line width change of a resist pattern due to variation in the post exposure delay time before electron beam irradiation and the post exposure delay time after electron beam irradiation can be inhibited, and it becomes excellent in process stability.

Such an acid diffusion controller (E) is exemplified by an electron beam radiation degradable basic compound such as a nitrogen atom-containing basic compound, a basic sulfonium compound and a basic iodonium compound. The acid diffusion controller can be used alone or in combination of two or more kinds.

The above nitrogen-containing organic compound can be exemplified by a compound represented by the following general formula (10):

(10)

(hereinafter, referred to as "nitrogen-containing compound (I)"), a diamino compound having two nitrogen atoms within the same molecule (hereinafter, referred to as "nitrogen-containing compound (II)"), a polyamino compound or polymer having three or more nitrogen atoms (hereinafter, referred to as "nitrogen-containing compound (III)"), an amide group-containing compound, a urea compound, a nitrogen-containing heterocyclic compound, and the like. In addition, the above acid diffusion controller may be used alone as one kind or may be used in combination of two or more kinds.

In the above general formula (10), $R^{61}$, $R^{62}$ and $R^{63}$ mutually independently represent a hydrogen atom, a linear, branched or cyclic alkyl group, an aryl group, or an aralkyl group. Also, the above alkyl group, aryl group, or aralkyl group may be unsubstituted or may be substituted with the other functional group such as a hydroxyl group. Here, the above linear, branched or cyclic alkyl group is exemplified by ones of 1 to 15, preferably 1 to 10 carbons, and specifically exemplified by a methyl group, an ethyl group, an n-propyl group, an isopropyl group, an n-butyl group, an isobutyl group, a sec-butyl group, a t-butyl group, an n-pentyl group, a neopentyl group, an n-hexyl group, a texyl group, an n-heptyl group, an n-octyl group, an n-ethylhexyl group, an n-nonyl group, an n-decyl group, and the like. Moreover, the above aryl group is exemplified by ones of 6 to 12 carbons, and specifically exemplified by a phenyl group, a tolyl group, a xylyl group, a cumenyl group, a 1-naphthyl group, and the like. Furthermore, the above aralkyl group is exemplified by ones of 7 to 19, preferably 7 to 13 carbons, and specifically exemplified by a benzyl group, an α-methylbenzyl group, a phenethyl group, a naphthyl group and the like.

The above nitrogen-containing compound (I) can specifically be exemplified by mono(cyclo)alkylamines such as n-hexylamine, n-heptylamine, n-octylamine, n-nonylamine, n-decylamine, n-dodecylamine and cyclohexylamine; di(cyclo)alkylamines such as di-n-butylamine, di-n-pentylamine, di-n-hexylamine, di-n-heptylamine, di-n-octylamine, di-n-nonylamine, di-n-decylamine, methyl-n-dodecylamine, di-n-dodecylmethyl, cyclohexylmethylamine and dicyclohexylamine; tri(cyclo)alkylamines such as triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, dimethyl-n-dodecylamine, di-n-dodecylmethylamine, dicyclohexylmethylamine and tricyclohexylamine; alkanolamines such as monoethanolamine, diethanolamine and triethanolamine; aromatic amines such as aniline, N-methylaniline, N,N-dimethylaniline, 2-methylaniline, 3-methylaniline, 4-methylaniline, 4-nitroaniline, diphenylamine, triphenylamine and 1-naphthylamine, and the like.

The above nitrogen-containing compound (II) can specifically be exemplified by ethylenediamine, N,N,N',N'-tetramethylethylenediamine, N,N,N',N'-tetrakis(2-hydroxypropyl)ethylenediamine, tetramethylenediamine, hexamethylenediamine, 4,4'-diaminodiphenylmethane, 4,4'-diaminodiphenylether, 4,4'-diaminobenzophenone, 4,4'-diaminodiphenylamine, 2,2-bis(4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis[1-(4-aminophenyl)-1-methylethyl]benzene, 1,3-bis[1-(4-aminophenyl)-1-methylethyl]benzene and the like.

The above nitrogen-containing compound (III) can specifically be exemplified by polyethyleneimine, polyarylamine, a polymer of N-(2-dimethylaminoethyl)acrylamide, and the like.

The above amide group-containing compound can specifically be exemplified by formamide, N-methylformamide, N,N-dimethylformamide, acetamide, N-methylacetamide, N,N-dimethylacetamide, propionamide, benzamide, pyrrolidon, N-methylpyrrolidon and the like.

The above urea compound can specifically be exemplified by urea, methylurea, 1,1-dimethylurea, 1,3-dimethylurea, 1,1,3,3-tetramethylurea, 1,3-diphenylurea, tri-n-butylthiourea and the like.

The above nitrogen-containing heterocyclic compound can specifically be exemplified by imidazoles such as imidazole, benzimidazole, 4-methylimidazole, 4-methyl-2-phenylimidazole and 2-phenylbenzimidazole; pyridines such as pyridine, 2-methylpyridine, 4-methylpyridine, 2-ethylpyridine, 4-ethylpyridine, 2-phenylpyridine, 4-phenylpyridine, 2-methyl-4-phenylpyridine, nicotine, nicotinic acid, amide nicotinate, quinoline, 8-oxyquinoline and acridine; and pyrazine, pyrazole, pyridazine, quinozaline, purine, pyrrolidine, piperidine, morpholine, 4-methylmorpholine, piperazine, 1,4-dimethylpiperazine, 1,4-diazabicyclo[2.2.2]octane and the like.

Also, the above basic compound degradable by exposure can be exemplified by a sulfonium compound represented by the following general formula (11-1):

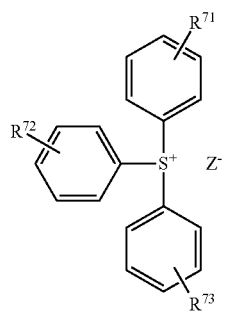

(11-1)

an iodonium compound represented by the following general formula (11-2):

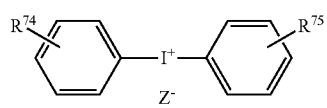

(11-2)

and the like.

In the above general formulae (11-1) and (11-2), $R^{71}$, $R^{72}$, $R^{73}$, $R^{74}$ and $R^{75}$ mutually independently represent a hydrogen atom, an alkyl group of 1 to 6 carbons, an alkoxyl group of 1 to 6 carbons, a hydroxyl group or a halogen atom. $Z^-$ represents $HO^-$, $R\text{—}COO^-$ (provided that R represents an alkyl group of 1 to 6 carbons, an aryl group of 1 to 6 carbons or an alkaryl group of 1 to 6 carbons) or an anion represented by the following general formula (11-3):

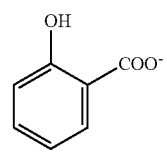

(11-3)

The above basic compound degradable by exposure is specifically exemplified by triphenylsulfonium hydroxide, triphenylsulfonium acetate, triphenylsulfonium salicylate, diphenyl-4-hydroxyphenylsulfonium hydroxide, diphenyl-4-hydroxyphenylsulfonium acetate, diphenyl-4-hydroxyphenylsulfonium salicylate, bis(4-t-butylphenyl)iodonium hydroxide, bis(4-t-butylphenyl)iodonium acetate, bis(4-t-butylphenyl)iodonium salicylate, 4-t-butylphenyl-4-hydroxyphenyliodonium hydroxide, 4-t-butylphenyl-4-hydroxyphenyliodonium acetate, 4-t-butylphenyl-4-hydroxyphenyliodonium salicylate and the like.

The compounding amount of the acid diffusion controller (E) is preferably 0.001 to 50% by weight of the total weight of solid component, more preferably 0.001 to 10% by weight, further preferably 0.001 to 5% by weight, and particularly preferably 0.001 to 3% by weight. Within the above range, a decrease in resolution, and deterioration of pattern shape, dimension fidelity and the like can be prevented. Moreover, even though the post exposure delay time from electron beam irradiation to heating after radiation irradiation becomes longer, the shape of the pattern upper layer portion is not deteriorated. Also, when the compounding amount is not more than 10% by weight, a decrease in sensitivity, developability of the unexposed portion and the like can be prevented. In addition, by using such an acid diffusion controller, storage stability of a positive type radiation-sensitive composition improves, resolution also improves, line width change of a resist pattern due to variation in the post exposure delay time before radiation irradiation and the post exposure delay time after radiation irradiation can be inhibited, and it becomes extremely excellent in process stability.

To the positive type radiation-sensitive composition of the invention, within the range of not inhibiting the purpose of the invention, if required, as the other component (F), one kind or two kinds or more of various additive agents such as a. dissolution promotor, b. dissolution controller, c. sensitizer, d. surfactant, e. organic carboxylic acid or oxo acid of phosphorus, or f. derivative thereof can be added.

a. Dissolution Promotor

The low molecular weight dissolution promotor is a component having a function of increasing the dissolvability to moderately increase the dissolution rate of a cyclic compound upon development when dissolvability of a resist base material in a developing solution such as an alkali is too low, and can be used within the range of not deteriorating the effect of the invention. The above dissolution promotor can be exemplified by a low molecular weight phenolic compound, and can be exemplified by bisphenols, tris(hydroxyphenyl)methane and the like. These dissolution promotors can be used alone or in mixture of two or more kinds. The compounding amount of the dissolution promotor, which is arbitrarily adjusted depending on the kind of a resist base material to be used, is 0 to 100 parts by weight per 100 parts by weight of a resist base material (compound (B), hereinafter, referred to as a resist base material (R)), preferably 0 to 30 parts by weight, more preferably 0 to 10 parts by weight, and further preferably 0 to 2 parts by weight.

b. Dissolution Controller

The dissolution controller is a component having a function of controlling the dissolvability to moderately decrease the dissolution rate upon development, when dissolvability of a resist base material in a developing solution such as an alkali is too high. As such a dissolution controller, ones not chemically changing in steps such as calcination, radiation irradiation and development of a resist coat, are preferable. The dissolution controller can be exemplified by aromatic hydrocarbons such as naphthalene, phenanthrene, anthracene and acenaphthene; ketones such as acetophenone, benzophenone and phenyl naphtyl ketone; sulfones such as methyl phenyl sulfone, diphenyl sulfone and dinaphthyl sulfone, and the like. These dissolution controllers can be used alone or in two or more kinds.

The compounding amount of the dissolution controller, which is arbitrarily adjusted depending on the kind of a resist base material (R) to be used, is 0 to 100 parts by weight per 100 parts by weight of the resist base material (R), preferably 0 to 30 parts by weight, more preferably 0 to 10 parts by weight, and further preferably 0 to 2 parts by weight.

c. Sensitizer

The sensitizer is a component having a function of absorbing irradiated radiation energy, transmitting the energy to the acid generator (D) and thereby increasing the acid generation amount, and improving the apparent sensitivity of a resist. Such a sensitizer can be exemplified by, but not particularly limited to, benzophenones, biacetyls, pyrenes, phenothiazines, fluorenes and the like.

These sensitizers can be used alone or in two or more kinds. The compounding amount of the sensitizer, which is arbitrarily adjusted depending on the kind of a resist base material (R) to be used, is 0 to 100 parts by weight per 100 parts by weight of the resist base material (R), preferably 0 to 30 parts by weight, more preferably 0 to 10 parts by weight, and further preferably 0 to 2 parts by weight.

d. Surfactant

The surfactant is a component having a function of improving coatability and striation of the positive type radiation-sensitive composition of the invention, developability of a resist and the like. Such a surfactant may be any of anionic, cationic, nonionic or amphoteric. A preferable surfactant is a nonionic surfactant. The nonionic surfactant has good affinity with a solvent used in production of a positive type radiation-sensitive composition and is more effective. Examples of the nonionic surfactant include, but not particularly limited to, polyoxyethylene higher alkyl ethers, polyoxyethylene higher alkyl phenyl ethers, higher fatty acid diesters of polyethylene glycol, and the like. The commercially available product can be exemplified by, hereinafter by trade name, EFTOP (manufactured by Jemco), MEGAFAC (manufactured by DIC), Fluorad (manufactured by Sumitomo 3M), AsahiGuard, Surflon (hereinbefore, manufactured by Asahi Glass), Pepole (manufactured by TOHO Chemical Industry), KP (manufactured by Shin-Etsu Chemical), Polyflow (manufactured by Kyoeisha Chemical) and the like.

The compounding amount of the surfactant, which is arbitrarily adjusted depending on the kind of a resist base material (R) to be used, is 0 to 100 parts by weight per 100 parts by weight of the resist base material (R), preferably 0 to 30 parts by weight, more preferably 0 to 10 parts by weight, and further preferably 0 to 2 parts by weight.

e. Organic Carboxylic Acid, or Oxo Acid of Phosphorus or Derivative Thereof

For the purposes of prevention of sensitivity deterioration or improvement of resist pattern shape, post exposure delay stability and the like, as an optional component, organic carboxylic acid, or oxo acid of phosphorus or derivative thereof can be contained. In addition, it can be used in combination with the acid diffusion controller, or may be used alone. The organic carboxylic acid is preferably exemplified by malonic acid, citric acid, malic acid, succinic acid, benzoic acid, salicylic acid, and the like. The oxo acid of phosphorus or the derivative thereof is exemplified by phosphoric acid or derivative thereof such as ester including phosphoric acid, di-n-butyl phosphate ester and diphenyl phosphate ester; phosphonic acid or derivative thereof such as ester including phosphonic acid, dimethyl phosphonate ester, di-n-butyl phosphonate ester, phenylphosphonic acid, diphenyl phosphonate ester and dibenzyl phosphonate ester; and phosphinic acid and derivative thereof such as ester including phosphinic acid and phenylphosphinic acid, and phosphonic acid is particularly preferable among them.

The organic carboxylic acid, or the oxo acid of phosphorous or the derivative thereof can be used alone or in combination of two or more kinds. The compounding amount of the organic carboxylic acid, or the oxo acid of phosphorous or the derivative thereof, which is arbitrarily adjusted depending on the kind of a resist base material (R) to be used, is 0 to 100 parts by weight per 100 parts by weight of the resist base material (R), preferably 0 to 30 parts by weight, more preferably 0 to 10 parts by weight, and further preferably 0 to 2 parts by weight.

f. Other Additive Agent Other Than the Above Dissolution Controller, Sensitizer, Surfactant, and Organic Carboxylic Acid, or Oxo Acid of Phosphorous or Derivative Thereof Further, to the positive type radiation-sensitive composition of the invention, one kind or two kinds or more of additive agents other than the above dissolution controller, sensitizer and surfactant, if required, can be compounded within the range of not inhibiting the purpose of the invention. Such an additive agent is exemplified by a dye, a pigment, an adhesion aid and the like. For example, by compounding a dye or a pigment, a latent image of the exposed portion can be visualized and influence of halation upon exposure can be alleviated, which is preferable. Moreover, by compounding an adhesion aid, adhesion to a substrate can be improved, which is preferable. Furthermore, other additive agents can include a halation preventing agent, a storage stabilizing agent, a defoaming agent, a shape improving agent and the like, specifically 4-hydroxy-4'-methylchalkone and the like.

The compounding ratio of the positive type radiation-sensitive composition of the invention (resist base material (R)/acid generator (D)/acid diffusion controller (E)/other component (F)) is, in % by weight based on solid content, preferably 10 to 90/0.001 to 50/0.01 to 50/0 to 50, more preferably 30 to 90/0.001 to 50/0.01 to 5/0 to 15, further preferably 58.5 to 80/10 to 37.5/0.01 to 3/0 to 1, and particularly preferably 70 to 75/10 to 30/0.01 to 3/0. With the above composition, it is excellent in performance such as sensitivity, resolution and alkaline developability.

The positive type radiation-sensitive composition of the invention is normally prepared by dissolving each component in a solvent into a homogenous solution upon use, and then, if required, filtering through a filter with a pore diameter of about 0.2 μm and the like, for example.

The above solvent used in preparing the positive type radiation-sensitive composition of the invention can be exemplified by, but not particularly limited to, ethylene glycol monoalkyl ether acetates such as ethylene glycol monomethyl ether acetate, ethylene glycol monoethyl ether acetate, ethylene glycol mono-n-propyl ether acetate and ethylene glycol mono-n-butyl ether acetate; ethylene glycol monoalkyl ethers such as ethylene glycol monomethyl ether and ethylene glycol monoethyl ether; propylene glycol monoalkyl ether acetates such as propylene glycol monomethyl ether acetate, propylene glycol monoethyl ether acetate, propylene glycol mono-n-propyl ether acetate and propylene glycol mono-n-butyl ether acetate; propylene glycol monoalkyl ethers such as propylene glycol monomethyl ether and propylene glycol monoethyl ether; ester lactates such methyl lactate, ethyl lactate, n-propyl lactate, n-butyl lactate and n-amyl lactate; aliphatic carboxylic acid esters such as methyl acetate, ethyl acetate, n-propyl acetate, n-butyl acetate, n-amyl acetate, n-hexyl acetate, methyl propionate and ethyl propionate; other esters such as methyl 3-methoxypropionate, ethyl 3-methoxypropionate, methyl 3-ethoxypropionate, ethyl 3-ethoxypropionate, methyl 3-methoxy-2-methylpropionate, 3-methoxybutylacetate, 3-methyl-3-methoxybutylacetate, butyl 3-methoxy-3-methylpropionate, butyl 3-methoxy-3-methylbutyrate, methyl acetoacetate, methyl pyruvate and ethyl pyruvate; aromatic hydrocarbons such as toluene and xylene; ketones such as 2-heptanone, 3-heptanone, 4-heptanone, cyclopentanone and cyclohexanone; amides such as N,N-dimethylformamide, N-methylacetamide, N,N-dimethylacetamide and N-methylpyrrolidone; lactones such as γ-lactone, and the like. These solvents can be used alone or in two or more kinds.

The radiation-sensitive composition of the invention can contain a resin soluble in an alkaline aqueous solution within the range of not inhibiting the purpose of the invention. The resin soluble in an alkaline aqueous solution is exemplified by novolac resin, polyvinyl phenols, polyacrylic acid, polyvinyl alcohol, styrene-maleic anhydride resin, and polymer containing acrylic acid, vinyl alcohol or vinylphenol as a monomeric unit, or derivatives thereof and the like. The compounding amount of the resin soluble in an alkaline aqueous solution, which is arbitrarily adjusted depending on the kind of a cyclic compound to be used, is preferably 0 to 30 parts by weight per 100 parts by weight of the above cyclic compound, more preferably 0 to 10 parts by weight, further preferably 0 to 5 parts by weight, and particularly preferably 0 part by weight.

[Resist Pattern Formation Method]

The invention relates to a resist pattern formation method including steps of forming a resist film on a substrate using the above positive type radiation-sensitive composition of the invention, exposing the resist film, and developing the resist film to form a resist pattern. The resist pattern obtained by the invention can also be formed as an upper layer resist in the multilayer resist process.

In order to form a resist pattern, a resist film is formed by coating the above positive type radiation-sensitive composition of the invention onto a conventionally and publicly known substrate using coating means such as spin coating, flow casting coating and roll coating. The conventionally and publicly known substrate can be exemplified by, but not particularly limited to, a substrate for electronic component, the same having a predetermined wiring pattern formed thereon, and the like. More specifically, it is exemplified by substrates made of metals such as silicon wafer, copper, chromium, iron and aluminum, a glass substrate and the like. The wiring pattern material is exemplified by copper, aluminum, nickel, gold and the like. Also, if required, it may be the substrate described above having an inorganic and/or organic coating provided thereon. The inorganic coating is exemplified by an inorganic bottom anti-reflective coating (inorganic BARC). The organic coating is exemplified by an organic bottom anti-reflective coating (organic BARC). Surface treatment with hexamethylene disilazane and the like may be conducted.

If required, the coated substrate is heated. The heating condition varies depending on the composition of the positive type radiation-sensitive composition, but is preferably 20 to 250° C., more preferably 20 to 150° C. By heating, adhesion of a resist to a substrate may improve, which is preferable.

Next, a resist film is exposed to a desired pattern by any radiation selected from the group consisting of visible light, ultraviolet light, excimer laser, electron beam, extreme ultraviolet light (EUV), X-ray and ion beam. The exposure condition and the like are arbitrarily selected depending on the composition of the positive type radiation-sensitive composition, and the like. In the invention, in order to stably form a fine pattern with a high degree of accuracy in exposure, it is preferable to heat after radiation irradiation. The heating condition varies depending on the composition of the positive type radiation-sensitive composition and the like, but is preferably 20 to 250° C., more preferably 20 to 150° C.

Thereafter, by developing the exposed resist film in an alkaline developing solution, a predetermined resist pattern is formed. As the above alkaline developing solution, for example, an alkaline aqueous solution having one kind or more of alkaline compounds such as mono-, di- or tri-alkylamines, mono-, di- or tri-alkanolamines, heterocyclic amines, tetramethyl ammonium hydroxide (TMAH) and choline dissolved such that the concentration is preferably 1 to 10% by mass, and more preferably 1 to 5% by mass can be used. When the concentration of the above alkaline aqueous solution is not more than 10% by mass, the exposed portion can be prevented from being dissolved in a developing solution, which is preferable.

Moreover, to the above alkaline developing solution, alcohols such as methanol, ethanol and isopropyl alcohol and the above surfactant can also be added in an adequate amount. Among them, it is particularly preferable to add isopropyl alcohol in 10 to 30% by mass. Thereby, wettability of a developing solution to a resist can be improved, which is preferable. In addition, when such a developing solution comprising an alkaline aqueous solution is used, washing with water is generally conducted after development.

After forming a resist pattern, a patterned wiring substrate is obtained by etching. Etching can be conducted by a publicly known method such as dry etching using plasma gas and wet etching with an alkaline solution, a cupric chloride solution, a ferric chloride solution and the like.

After forming a resist pattern, it is also possible to conduct plating. The above plating method is exemplified by copper plating, solder plating, nickel plating, gold plating and the like.

The remaining resist pattern after etching can be peeled with an organic solvent or an alkaline aqueous solution stronger than the alkaline aqueous solution used for development. The above organic solvent is exemplified by PGMEA (propylene glycol monomethyl ether acetate), PGME (propylene glycol monomethyl ether), EL (ethyl lactate) and the like, and the strong alkaline aqueous solution is exemplified by a 1 to 20% by mass sodium hydroxide aqueous solution and a 1 to 20% by mass potassium hydroxide aqueous solution. The above peeling method is exemplified by an immersion method, a spray method and the like. Moreover, a wiring substrate having a resist pattern formed may be a multilayer wiring substrate, or may have a small diameter through hole.

The wiring substrate obtained in the invention can also be formed by a method of forming a resist pattern, then depositing a metal in vacuum, and subsequently dissolving the resist pattern in a solution, i.e., a lift-off method.

EXAMPLES

Embodiments of the invention will be further specifically described with reference to examples below. However, the invention is not limited to these examples.

Synthesis Samples

Synthesis of Compound (A)

Synthesis Sample 1

Synthesis of CR-1

To a four neck flask (1000 ml) equipped with a dropping funnel, a Dimroth condenser tube, a thermometer and a stirring blade, sufficiently dried and substituted with nitrogen, resorcinol (22 g, 0.2 mol) manufactured by Kanto Chemical, 4-isopropylbenzaldehyde (29.6 g, 0.2 mol), and dehydrated ethanol (200 ml) were charged under a nitrogen gas stream to prepare an ethanol solution. This solution was heated to 85° C. with a mantle heater while stirring. Next, 75 ml of concentrated hydrochloric acid (35%) was dropped through the dropping funnel over 30 minutes, and continuously stirred at 85° C. for 3 hours. After the reaction terminated, it was stood to cool to reach room temperature, and then cooled in an ice bath. After keeping it to stand still for 1 hour, a pale yellow objective crude crystal was produced and filtered. The crude crystal was washed twice with 50 ml of methanol, separated, and vacuum dried to obtain an objective product (hereinafter, referred to as CR-1) (45.6 g, 95% yield).

The structure of this compound showed, as the result of analysis by LC-MS, that the molecular weight of the objective product was 960. The chemical shift values (δ ppm, TMS standard) of $^1$H-NMR in a heavy dimethyl sulfoxide solvent were 1.1 to 1.2 (m, 24H), 2.6 to 2.7 (m, 4H), 5.5 (s, 4H), 6.0 to 6.8 (m, 24H), 8.4 to 8.5 (d, 8H).

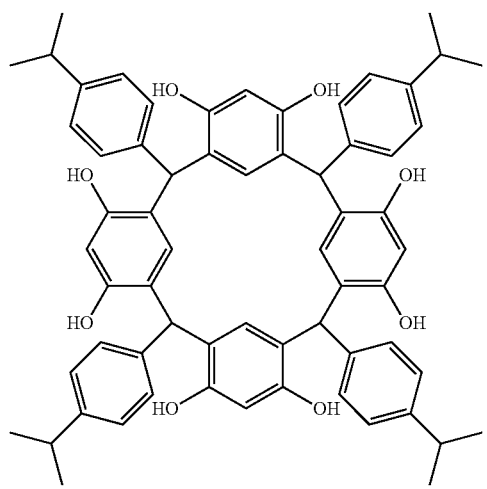

(CR-1)

Synthesis Sample 2

Synthesis of CR-1A-EE50

In a four neck flask (1000 ml) equipped with a dropping funnel, a Dimroth condenser tube, a thermometer and a stirring blade, sufficiently dried and substituted with nitrogen, to a solution comprising 9.6 g (10 mmol) of CR-1, 2.5 g of pyridinium p-toluenesulfonate and 400 ml of acetone, 2.9 g (40 mmol) of ethyl vinyl ether was dropped under a nitrogen gas stream. The reaction solution was stirred at room temperature for 24 hours. After the reaction terminated, a solvent was removed, and the obtained solid was purified by column chromatography using a mixed solvent of hexane/ethyl acetate=1/3. 9.2 g of CR-1A-EE50 having 50 mol % of hydrogen atom of a phenolic hydroxyl group substituted with an ethoxyethyl group was obtained.

The chemical shift values (δ ppm, TMS standard) of $^1$H-NMR of the obtained product in a heavy dimethyl sulfoxide solvent were 0.9 to 1.0 (m, 24H), 1.1 to 1.2 (m, 24H), 1.3 to 1.4 (m, 24H), 2.6 to 2.7 (m, 4H), 3.3 to 3.4 (m, 16H), 5.1 (m, 8H), 5.5 (s, 4H), 6.0 to 6.8 (m, 24H).

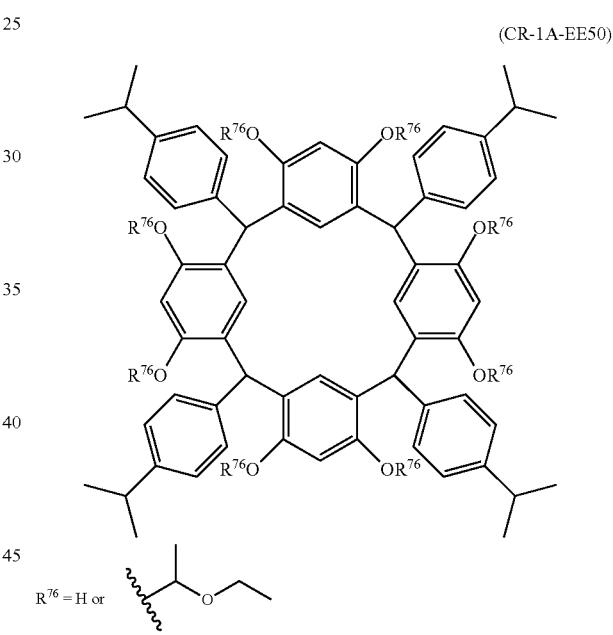

(However, 50 mol % of $R^{76}$ is an ethoxyethyl group.)

Synthesis Examples

Synthesis of Compound (B)

Synthesis Example 1

Synthesis of CR-1A-CHDVE25

In a four neck flask (1000 ml) equipped with a dropping funnel, a Dimroth condenser tube, a thermometer and a stirring blade, sufficiently dried and substituted with nitrogen, to a solution comprising 9.6 g (10 mmol) of CR-1 as the compound (A), 0.1 g of trifluoroacetic acid and 400 ml of 1,3-dioxolane, 3.92 g (20 mmol) of 1,4-divinyloxymethylcyclohexane was dropped under a nitrogen gas stream. Next, the reaction solution was stirred at room temperature for 24 hours. After the reaction terminated, a solvent was removed, and the obtained solid was purified by column chromatography using a mixed solvent of hexane/ethyl acetate=1/3. 10.2 g of CR-1A-CHDVE25 having an acid dissociable functional group introduced in 25 mol % of hydrogen atom of a phenolic hydroxyl group of CR-1 was obtained.

The chemical shift values (δ ppm, TMS standard) of $^1$H-NMR of the obtained CR-1A-CHDVE25 in a heavy dimethyl sulfoxide solvent confirmed that the ratio between the number of hydrogen atoms of a phenyl group and the number of hydrogen atoms of a phenolic hydroxyl group was 4:1 and that an acid dissociable functional group was introduced in 25 mol % of hydrogen atom of a phenolic hydroxyl group of CR-1.

The measurement result of GPC of CR-1A-CHDVE25 was Mw=2163. GPC was obtained by using "GPC SYSTEM-21" manufactured by Shimadzu as a GPC measuring apparatus, a refractive index detector (RI) as a detector, tetrahydrofuran (THF) as an eluting solution, and polystyrene standard conversion. As columns, two "Shodex KF-801" connected in series and "Shodex KF-802.5" manufactured by Showa Denko were used, and the conditions were a sample concentration of 0.5%, a sample injection amount of 400 μl, a column temperature of 40° C., an RI temperature of 40° C., a flow rate of an eluting solution of 1.0 ml/min, and an analysis time of 50 minutes.

Synthesis Example 2

Synthesis of CR-1A-TMA12.5

In a four neck flask (1000 ml) equipped with a dropping funnel, a Dimroth condenser tube, a thermometer and a stirring blade, sufficiently dried and substituted with nitrogen, a solution comprising 9.6 g (10 mmol) of CR-1 as the compound (A), 0.01 g of 4-dimethylaminopyridine and 400 ml of 1,3-dioxolane was ice cooled, and then a solution comprising 0.87 g (3.3 mmol) of 1,3,5-benzenetricarboxylic acid chloride as the compound (C) and 10 g of pyridine was dropped under a nitrogen gas stream. Then, the reaction solution was stirred for 15 minutes. After the reaction terminated, 10 ml of methanol was added, it was added to 1000 mL of 1N hydrochloric acid aqueous solution, and the obtained solid was filtered and purified by column chromatography using a mixed solvent of hexane/ethyl acetate=1/3. 10.0 g of CR-1A-TMA12.5 having an acid dissociable functional group introduced in 12.5 mol % of hydrogen atom of a phenolic hydroxyl group of CR-1 was obtained.

The chemical shift values (δ ppm, TMS standard) of $^1$H-NMR of the obtained CR-1A-TMA12.5 in a heavy dimethyl sulfoxide solvent confirmed that the ratio between the number of hydrogen atoms of a phenyl group and the number of hydrogen atoms of a phenolic hydroxyl group was 25:7 and that an acid dissociable functional group was introduced in 12.5 mol % of hydrogen atom of a phenolic hydroxyl group of CR-1.

The measurement result of GPC of CR-1A-TMA12.5 was Mw=1325.

Synthesis Example 3

Synthesis of CR-1A-mXG25

In a four neck flask (500 ml) equipped with a dropping funnel, a Dimroth condenser tube, a thermometer and a stirring blade, sufficiently dried and substituted with nitrogen, to a solution comprising m-xylene dimethanol (reagent manufactured by Aldrich; 27.6 g) and 198 ml of toluene, 36.0 g of trioxane was added under a nitrogen gas flow. Then, it was stirred, under ice cooling, while hydrogen chloride gas was blown for 2.5 hours. After the reaction terminated, blowing of hydrogen chloride gas was stopped, the temperature went back to room temperature, an insoluble layer was separated by a separating funnel, anhydrous sodium sulphate was added to a toluene layer, and it was stirred at room temperature and then subjected to filtering treatment. The solvent was removed from the obtained filtrate, and then 31.6 g of 1,3-bis[(chloromethoxy)methyl]benzene (mXG) represented by the following chemical formula was obtained by single distillation under reduced pressure.

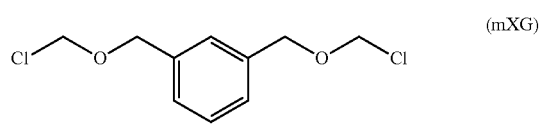 [SMILES: ClCOCc1cccc(COCCl)c1]

(mXG)

The chemical shift values (δ ppm, TMS standard) of $^1$H-NMR of the obtained product in a heavy chloroform solvent were 4.8 (s, 2H), 5.5 (s, 2H), and 7.2 to 7.4 (m, 4H). Moreover, by GC-MS, the molecular weight of the objective product was confirmed to be 234.

Next, in a four neck flask (1000 ml) equipped with a dropping funnel, a Dimroth condenser tube, a thermometer and a stirring blade, sufficiently dried and substituted with nitrogen, to a solution comprising 9.6 g (10 mmol) of CR-1 as the compound (A), 0.01 g of 4-dimethylaminopyridine and 400 ml of 1,3-dioxolane, a solution comprising 0.632 g (20 mmol) of mXG as the compound (C) and 10 g of pyridine was dropped under a nitrogen gas stream. Then, the reaction solution was stirred at room temperature for 24 hours. After the reaction terminated, 10 ml of methanol was added, it was added to 1000 mL of 1N hydrochloric acid aqueous solution, and the obtained solid was filtered and purified by column chromatography using a mixed solvent of hexane/ethyl acetate=1/3. 11.8 g of CR-1A-mXG25 having an acid dissociable functional group introduced in 25 mol % of hydrogen atom of a phenolic hydroxyl group of CR-1 was obtained.

The chemical shift values (δ ppm, TMS standard) of $^1$H-NMR of the obtained CR-1A-mXG25 in a heavy dimethyl sulfoxide solvent confirmed that the ratio between the number of hydrogen atoms of a phenyl group and the number of hydrogen atoms of a phenolic hydroxyl group was 4:1 and that an acid dissociable functional group was introduced in 25 mol % of hydrogen atom of a phenolic hydroxyl group of CR-1.

The measurement result of GPC of CR-1A-mXG25 was Mw=2025.

Examples 1 to 15 and Comparative Example 1

Positive type radiation-sensitive compositions were prepared by compounding components described in Table 1 into homogenous solutions and filtering them through a membrane filter made of Teflon (registered trademark) with a pore diameter of 0.1 μm, and the following evaluations were conducted for each. The results are shown in Table 3.

(1) Evaluation of Sensitivity

A resist was spin coated on a clean silicon wafer, and then prebaked (PB) before exposure in an oven to form a resist film with a thickness of 60 nm. The resist film was irradiated with electron beam with 100 nm interval and 1:1 line and space setting using an electron beam lithography system (ELS- 7500, manufactured by ELIONIX). After irradiation, it was heated at each predetermined temperature for 90 seconds, and developed in a 2.38% by weight TMAH aqueous solution for 60 seconds. Subsequently, it was washed with water for 30 seconds, and dried to form a positive type resist pattern. The obtained line and space was observed by a scanning electron microscope (S-4800 manufactured by Hitachi High-Technologies). In addition, the dose amount ($\mu C/cm^2$) in this regard was sensitivity.

A: dose amount≤50 $\mu C/cm^2$ (excellent sensitivity)
B: 50 $\mu C/cm^2$<dose amount≤120 $\mu C/cm^2$ (good sensitivity)
C: 120 $\mu C/cm^2$<dose amount (poor sensitivity)

(2) Evaluation of Line Edge Roughness (LER)

The distance between the edge and the standard line was measured using a Hitachi SEM Terminal PC V5 Offline Length Measuring Software for Semiconductor (manufactured by Hitachi Science Systems) for arbitrary 300 points in the length direction with 100 nm interval and 1:1 line and space. The standard deviation (3σ) was calculated from the measurement result.

A: LER (3σ)≤3.5 nm (good LER)
C: 3.5 nm<LER (3σ) (not good LER)

(3) Evaluation of Pattern Collapse

A resist pattern with 40 nm interval and 1:1 line and space was formed in an area of 1 $\mu m^2$ by the same method as (1) evaluation of sensitivity. The obtained line and space was observed by a scanning electron microscope (S-4800 manufactured by Hitachi High-Technologies).

A: no pattern collapse
C: pattern collapse present in part

From the results of the above (1) to (3), it was recognized that a positive type radiation-sensitive composition using the compound (B) of the invention had better sensitivity and LER than a positive type radiation-sensitive composition using a compound of Comparative Example, and could prevent collapse in a fine pattern.

TABLE 1

| | (B) Compound (g) | (D) Acid generator (g) | (E) Acid Diffusion Controller (g) | Solvent (g) |
|---|---|---|---|---|
| Example 1 | CR-1A-CHDVE25 1.00 | P-1 0.3 | Q-1 0.03 | S-1 30.0 |
| Example 2 | CR-1A-CHDVE25 1.00 | P-2 0.3 | Q-1 0.03 | S-1 30.0 |
| Example 3 | CR-1A-CHDVE25 1.00 | P-3 0.3 | Q-1 0.03 | S-1 30.0 |
| Example 4 | CR-1A-CHDVE25 1.00 | P-4 0.3 | Q-1 0.03 | S-1 30.0 |
| Example 5 | CR-1A-CHDVE25 1.00 | P-4 0.3 | Q-1 0.03 | S-2 30.0 |
| Example 6 | CR-1A-TMA12.5 1.00 | P-1 0.3 | Q-1 0.03 | S-1 30.0 |
| Example 7 | CR-1A-TMA12.5 1.00 | P-2 0.3 | Q-1 0.03 | S-1 30.0 |
| Example 8 | CR-1A-TMA12.5 1.00 | P-3 0.3 | Q-1 0.03 | S-1 30.0 |
| Example 9 | CR-1A-TMA12.5 1.00 | P-4 0.3 | Q-1 0.03 | S-1 30.0 |
| Example 10 | CR-1A-TMA12.5 1.00 | P-4 0.3 | Q-1 0.03 | S-2 30.0 |
| Example 11 | CR-1A-mXG25 1.00 | P-1 0.3 | Q-1 0.03 | S-1 30.0 |
| Example 12 | CR-1A-mXG25 1.00 | P-2 0.3 | Q-1 0.03 | S-1 30.0 |
| Example 13 | CR-1A-mXG25 1.00 | P-3 0.3 | Q-1 0.03 | S-1 30.0 |
| Example 14 | CR-1A-mXG25 1.00 | P-4 0.3 | Q-1 0.03 | S-1 30.0 |
| Example 15 | CR-1A-mXG25 1.00 | P-4 0.3 | Q-1 0.03 | S-2 30.0 |
| Comparative Example 1 | CR-1A-EE50 1.00 | P-1 0.3 | Q-1 0.03 | S-1 30.0 |

(D) Acid generator
P-1: Triphenylbenzenesulfonium trifluoromethanesulfonate (Midori Kagaku)
P-2: Triphenylbenzenesulfonium nonafluorobutanesulfonate (Midori Kagaku)
P-3: Diphenylbenzeneiodonium trifluoromethanesulfonate (Midori Kagaku)
P-4: Diphenylbenzeneiodonium nonafluorobutanesulfonate (Midori Kagaku)
(E) Acid Diffusion Controller
Q-1: Trioctylamine (Tokyo Chemical Industry)
Solvent
S-1: Propylene glycol monomethyl ether (Tokyo Chemical Industry)
S-2: Propylene glycol monomethyl ether acetate (Tokyo Chemical Industry)

TABLE 1

| | PEB* (° C.) | Sensitivity | LER (3σ) | Pattern Collapse |
|---|---|---|---|---|
| Example 1 | 110 | A | A | A |
| Example 2 | 110 | A | A | A |
| Example 3 | 110 | A | A | A |
| Example 4 | 110 | A | A | A |
| Example 5 | 110 | A | A | A |
| Example 6 | 110 | A | A | A |
| Example 7 | 110 | A | A | A |
| Example 8 | 110 | A | A | A |
| Example 9 | 110 | A | A | A |
| Example 10 | 110 | A | A | A |
| Example 11 | 110 | A | A | A |
| Example 12 | 110 | A | A | A |
| Example 13 | 110 | A | A | A |
| Example 14 | 110 | A | A | A |
| Example 15 | 110 | A | A | A |
| Comparative Example 1 | 110 | A | C | C |

*PEB: Temperature for heating after electron beam irradiation

According to the invention, it is possible to provide a compound having high dissolvability in a safe solvent and capable of preventing collapse of the resultant resist pattern and also reducing roughness of the resist pattern, a radiation-sensitive composition containing the same, and a resist pattern formation method using the radiation-sensitive composition.

What is claimed is:

1. A positive type radiation-sensitive composition comprising a compound (B), an acid generator (D) generating acid directly or indirectly by irradiation of any radiation selected from the group consisting of visible light, ultraviolet light, excimer laser, electron beam, extreme ultraviolet light (EUV), X-ray and ion beam, an acid diffusion controller (E), and a solvent, wherein the compound (B) is obtained by reaction between a polyphenol based cyclic compound (A) represented by the following formula (1-2) and a compound (C) represented by the following formula (3):

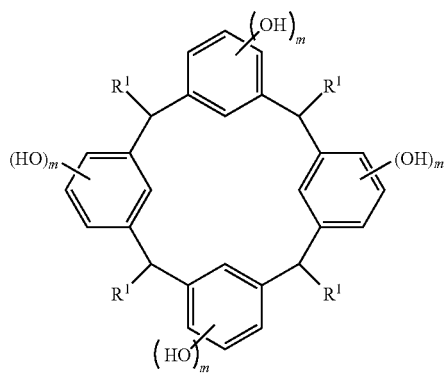

(1-2)

(In the formula (1), R¹ is independently an alkyl group of 1 to 20 carbons, or a group represented by the following formula (2),

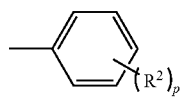

(2)

wherein, R² is independently a functional group selected from the group consisting of a hydrogen atom, a cycloalkyl group of 3 to 20 carbons, an aryl group of 6 to 20 carbons, an alkoxy group of 1 to 20 carbons, a hydroxyl group, a cyano group, a nitro group, a heterocyclic group, a halogen atom and an alkylsilyl group of 1 to 20 carbons, or an acid dissociable functional group selected from the group consisting of a substituted methyl group of 2 to 20 carbons, a 1-substituted ethyl group of 3 to 20 carbons, a 1-substituted-n-propyl group of 4 to 20 carbons, a 1-branched alkyl group of 3 to 20 carbons, a silyl group of 1 to 20 carbons, an acyl group of 2 to 20 carbons, a 1-substituted alkoxyalkyl group of 2 to 20 carbons, a cyclic ether group of 2 to 20 carbons, alkoxycarbonyl group of 2 to 20 carbons and an alkoxycarbonylalky group, m is an integer of 1 to 4, provided that the compound (A) has at least one phenolic hydroxyl group or carboxyl group)

$$A\text{--}(B)_q \qquad (3)$$

(In the formula (3), A is an aliphatic hydrocarbon group of 1 to 18 carbons, an alicyclic hydrocarbon group of 3 to 18 carbons or an aromatic hydrocarbon group of 6 to 24 carbons, B is an acid crosslinkable reactive group, and q is an integer of 2 to 4).

2. A positive type radiation-sensitive composition according to claim 1, wherein the acid crosslinkable reactive group is any one selected from the group consisting of a vinyloxy group, a halomethyl group, a halocarbonyl group and a carboxyl group.

3. A positive type radiation-sensitive composition according to claim 1, wherein the compound (A) is a compound represented by the following formula (1-3):

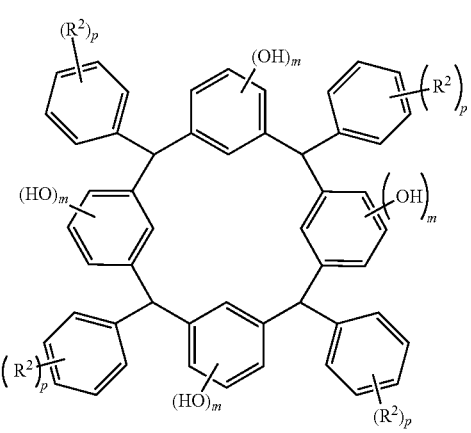

(1-3)

(In the formula (1-3), R², m and p are the same as above).

4. A positive type radiation-sensitive composition according to claim 3, wherein the compound (A) is a compound represented by the following formula (1-4) or (1-5):

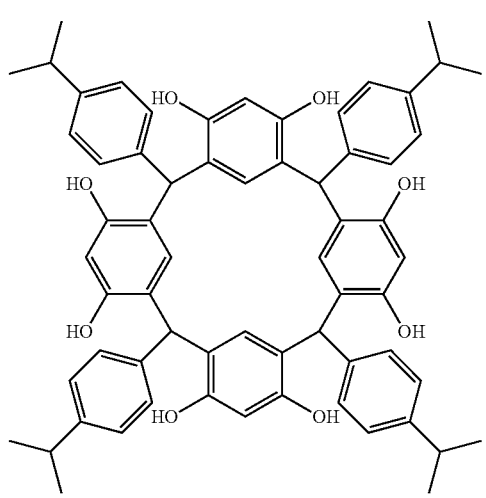

(1-4)

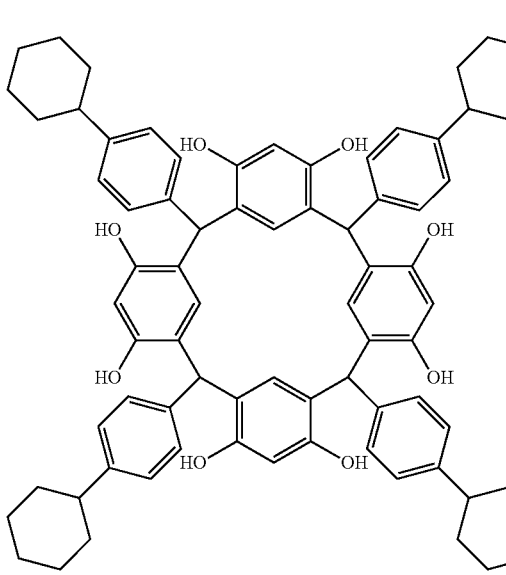

(1-5)

5. A positive type radiation-sensitive composition according to claim 1, wherein the compound (C) is any compound selected from the compound group represented by the following formula (3-1):

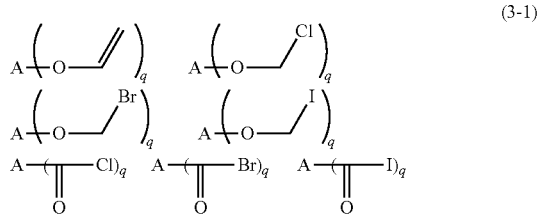

(3-1)

(In the formula (3-1), A and q are the same as above).

6. A positive type radiation-sensitive composition according to claim 1, wherein the compound (C) is any compound selected from the compound group represented by the following formula (3-2):

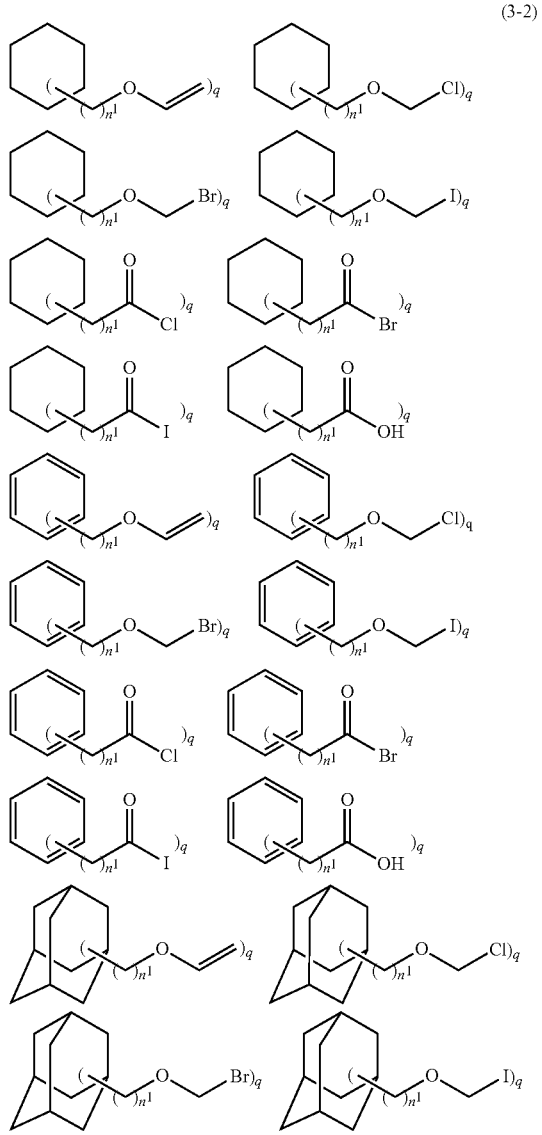

(3-2)

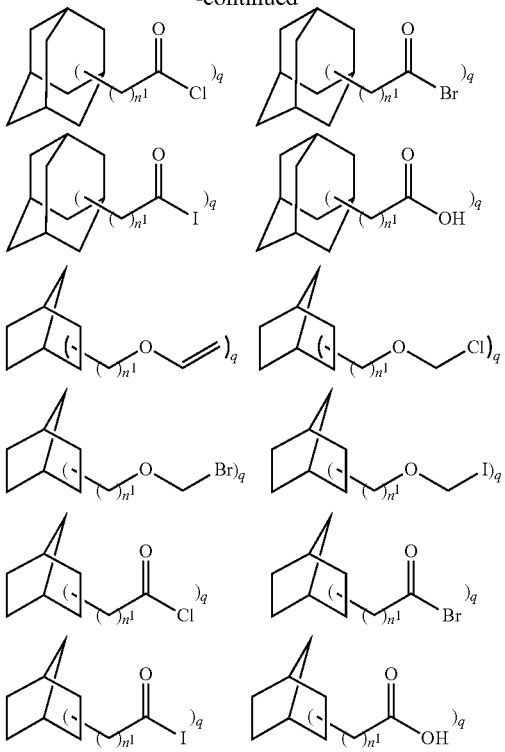

(In the formula (3-2), $n^1$ is an integer of 0 to 2, and q is an integer of 2 to 4).

7. A positive type radiation-sensitive composition according to claim 6, wherein the compound (C) is any compound selected from the compound group represented by the following formula (3-3):

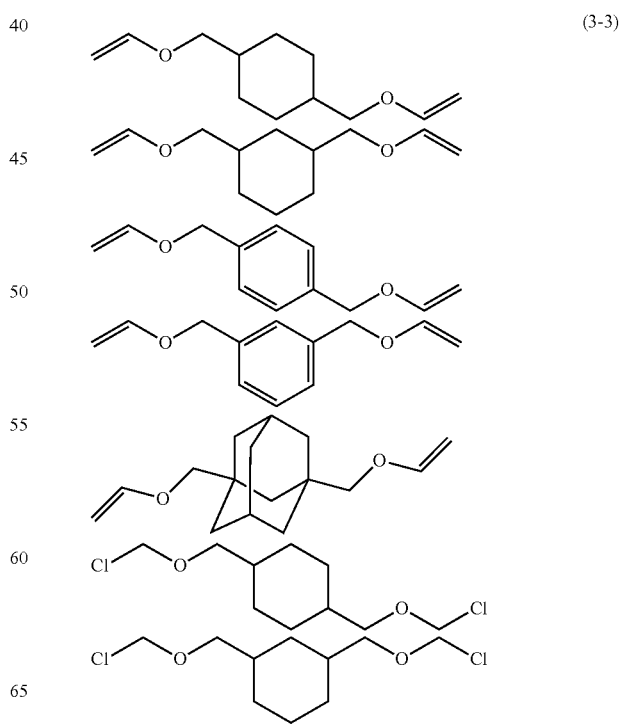

(3-3)

-continued

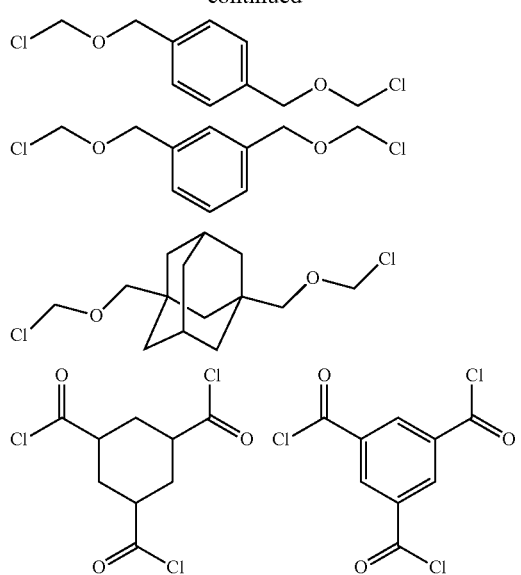

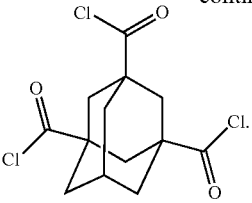

8. A positive type radiation-sensitive composition according to claim 1, comprising 1 to 80% by weight of solid component and 20 to 99% by weight of solvent.

9. A resist pattern formation method comprising steps of forming a resist film on a substrate using a positive type radiation-sensitive composition according to claim 1, exposing the resist film, and developing the resist film to form a resist pattern.

10. A resist pattern formation method comprising steps of forming a resist film on a substrate using a positive type radiation-sensitive composition according to claim 8, exposing the resist film, and developing the resist film to form a resist pattern.

* * * * *